United States Patent
Herrema et al.

(10) Patent No.: US 11,459,590 B2
(45) Date of Patent: *Oct. 4, 2022

(54) POLYHYDROXYALKANOATE PRODUCTION METHODS AND SYSTEMS FOR SAME

(71) Applicant: Newlight Technologies, Inc., Huntington Beach, CA (US)

(72) Inventors: Markus Donald Herrema, Venice, CA (US); Kenton Kimmel, Dana Point, CA (US)

(73) Assignee: Newlight Technologies, Inc., Huntington Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/710,516

(22) Filed: Dec. 11, 2019

(65) Prior Publication Data

US 2020/0190544 A1 Jun. 18, 2020

Related U.S. Application Data

(63) Continuation of application No. 15/849,193, filed on Dec. 20, 2017, now Pat. No. 10,538,792, which is a continuation of application No. 14/526,228, filed on Oct. 28, 2014, now Pat. No. 9,850,508, which is a continuation of application No. 14/286,274, filed on May 23, 2014, now abandoned, which is a continuation of application No. 13/310,542, filed on Dec. 2, 2011, now Pat. No. 8,735,113.

(51) Int. Cl.
| | |
|---|---|
| C12P 7/625 | (2022.01) |
| A61K 38/05 | (2006.01) |
| C08G 63/06 | (2006.01) |
| C12N 1/30 | (2006.01) |
| C12P 7/42 | (2006.01) |
| C12P 7/62 | (2022.01) |
| F02D 17/02 | (2006.01) |
| C12M 1/00 | (2006.01) |
| C10L 3/10 | (2006.01) |
| C12M 1/04 | (2006.01) |

(52) U.S. Cl.
CPC ............. *C12P 7/625* (2013.01); *A61K 38/05* (2013.01); *C08G 63/06* (2013.01); *C10L 3/10* (2013.01); *C12M 1/04* (2013.01); *C12M 47/18* (2013.01); *C12N 1/30* (2013.01); *C12P 7/42* (2013.01); *C12P 7/62* (2013.01); *F02D 17/02* (2013.01)

(58) Field of Classification Search
CPC .................................................... C12P 7/625
See application file for complete search history.

(56) References Cited

U.S. PATENT DOCUMENTS

| | | |
|---|---|---|
| 3,878,305 A | 4/1975 | Damico et al. |
| 4,101,533 A | 7/1978 | Lafferty et al. |
| 4,375,515 A | 3/1983 | Patel et al. |
| 4,433,053 A | 2/1984 | Hughes et al. |
| 4,524,569 A | 6/1985 | Hanna |
| 4,562,245 A | 12/1985 | Stageman |
| 4,968,611 A | 11/1990 | Traussnig et al. |
| 5,344,766 A | 9/1994 | Ramachandran et al. |
| H1430 H | 4/1995 | Apel et al. |
| 5,434,062 A | 7/1995 | Groleau et al. |
| 5,480,794 A | 1/1996 | Peoples et al. |
| 5,487,834 A | 6/1996 | Carman et al. |
| 5,642,630 A | 7/1997 | Abdelmalek et al. |
| 5,727,903 A | 3/1998 | Borray et al. |
| 5,747,584 A | 5/1998 | Noda |
| 5,789,536 A | 6/1998 | Liggat et al. |
| 5,842,357 A | 12/1998 | Siwajek et al. |
| 5,849,894 A | 12/1998 | Clemente et al. |
| 5,871,980 A | 2/1999 | Naylor et al. |
| 5,894,062 A | 4/1999 | Liddel |
| 5,942,597 A | 8/1999 | Noda et al. |
| 6,043,063 A | 3/2000 | Kurdikar et al. |
| 6,051,411 A | 4/2000 | Turtakovsky et al. |
| 6,205,704 B1 | 3/2001 | Schmitz et al. |
| 6,395,520 B1 | 5/2002 | Babel et al. |
| 6,446,385 B1 | 9/2002 | Crutcher |

(Continued)

FOREIGN PATENT DOCUMENTS

| | | |
|---|---|---|
| JP | 2003-184575 | 7/2003 |
| WO | WO 99/57298 | 11/1999 |

(Continued)

OTHER PUBLICATIONS

How can livestock methane emissions be reduced? Ruminant Livestock (Mar. 2007). http://www.epa.gov/methane/rlep/faq.html.
Potential management practices and technologies for reducing methane emissions from agriculture. http://www.maf.govt.nz/mafnet/rural-nz/sustainable-resource-use/climate/green-house-gas-migration/ghg-mitigation-05.htm. Sep. 2001, p. 30-49.
Alvarado et al., Effects of natural porous additives on the tensile mechanical perforamnce and moisture absorption behavior of PHBV-based composites for construction, Stanford Undergraduate Research Journal, Spring 2011, vol. 10, pp. 30-35.
Asenjo et al. "Microbial conversion of methane into poly-beta-hydroxybutyrate (PHB) growth and intracellular product accumulation in a type II methanotroph" J. Ferment Technol., 1986, vol. 64, No. 4, pp. 271-278.
Bartle, "Exploring a Gaseating Bacteria," University of Bergen Magazine, 2002, at http://www.uib.no/elin/elpub/uibmag/en02/bacteria.htmle.

(Continued)

*Primary Examiner* — Rosanne Kosson
(74) *Attorney, Agent, or Firm* — Knobbe, Martens, Olson & Bear LLP

(57) ABSTRACT

Several embodiments of the invention relate generally to a system and methods for the treatment of gaseous emissions comprising methane and one or more non-methane compounds that can influence the metabolism of methane-oxidizing microorganisms. In several embodiments, there is provided a system and methods for the treatment of methane emissions through the use of methanotrophic microorganisms to generate functionally consistent and harvestable products. Certain embodiments of the invention are particularly advantageous because they reduce environmentally-destructive methane emissions and produce harvestable end-products.

18 Claims, No Drawings

(56) References Cited

U.S. PATENT DOCUMENTS

| | | |
|---|---|---|
| 6,472,188 B1 | 10/2002 | Lee et al. |
| 6,599,423 B2 | 7/2003 | Boles et al. |
| 6,666,027 B1 | 12/2003 | Cardenas, Jr. |
| 6,709,849 B2 | 3/2004 | Cheung |
| 6,749,368 B2 | 6/2004 | Ankeny et al. |
| 6,770,464 B2 | 8/2004 | Steinbuchel et al. |
| 6,982,161 B1 | 1/2006 | Herrema et al. |
| 7,098,298 B2 | 8/2006 | Kinoshita et al. |
| 7,141,400 B2 | 11/2006 | Yu |
| 7,226,765 B2 | 6/2007 | Narasimhan et al. |
| 7,410,717 B2 | 8/2008 | Moon et al. |
| 7,455,999 B2 | 11/2008 | Madison et al. |
| 7,504,556 B2 | 3/2009 | Madison et al. |
| 7,524,659 B2 | 4/2009 | Nomoto et al. |
| 7,527,963 B2 | 5/2009 | Nomoto et al. |
| 7,579,176 B2 | 8/2009 | Herrema et al. |
| 7,641,706 B1 | 1/2010 | McMurry et al. |
| 7,745,197 B1 | 6/2010 | Herrema et al. |
| 7,887,893 B2 | 2/2011 | Billington et al. |
| 8,030,021 B2 | 10/2011 | Criddle et al. |
| 8,071,342 B2 | 12/2011 | Herrema et al. |
| 8,177,870 B2 | 5/2012 | Herrema et al. |
| 8,263,373 B2 | 9/2012 | Herrema et al. |
| 8,465,876 B2 | 6/2013 | Herrema et al. |
| 8,703,470 B2 | 4/2014 | Herrema et al. |
| 8,735,113 B2 | 5/2014 | Herrema et al. |
| 8,930,236 B2 | 1/2015 | Gillenson et al. |
| 8,945,915 B2 | 2/2015 | Herrema et al. |
| 9,040,267 B2 | 5/2015 | Herrema |
| 9,085,784 B1 | 7/2015 | Herrema |
| 9,243,266 B2 | 1/2016 | Herrema et al. |
| 9,725,744 B2 | 8/2017 | Herrema |
| 9,850,508 B2 | 12/2017 | Herrema et al. |
| 9,868,967 B2 | 1/2018 | Herrema et al. |
| 10,378,030 B2 | 8/2019 | Herrema |
| 10,450,592 B2 | 10/2019 | Herrema |
| 10,494,652 B2 | 12/2019 | Herrema et al. |
| 10,538,792 B2 | 1/2020 | Herrema et al. |
| 2003/0004299 A1 | 1/2003 | Srienc et al. |
| 2005/0089740 A1 | 4/2005 | Moon et al. |
| 2007/0141660 A1 | 6/2007 | Chotani et al. |
| 2007/0161097 A1 | 7/2007 | Green et al. |
| 2007/0192221 A1 | 8/2007 | Sandor et al. |
| 2008/0160567 A1 | 7/2008 | Billington et al. |
| 2008/0160569 A1 | 7/2008 | Ho et al. |
| 2009/0176900 A1 | 7/2009 | Hirose et al. |
| 2009/0203093 A1 | 8/2009 | Steinbuchel et al. |
| 2009/0226962 A1 | 9/2009 | Huisman et al. |
| 2009/0301099 A1 | 12/2009 | Nigro |
| 2009/0317879 A1 | 12/2009 | Criddle et al. |
| 2010/0093043 A1 | 4/2010 | Huisman et al. |
| 2010/0190221 A1 | 7/2010 | Herrema et al. |
| 2010/0190224 A1 | 7/2010 | Poetter et al. |
| 2010/0255540 A2 | 10/2010 | Herrema et al. |
| 2010/0279180 A1 | 11/2010 | Herrema et al. |
| 2011/0112257 A1 | 5/2011 | Billington et al. |
| 2011/0112258 A1 | 5/2011 | Billington et al. |
| 2011/0146488 A1 | 6/2011 | Jacob |
| 2011/0159556 A1* | 6/2011 | Pieja ............... C12P 7/625 435/135 |
| 2011/0160067 A1 | 6/2011 | Sundstrom et al. |
| 2012/0028321 A1 | 2/2012 | Criddle et al. |
| 2012/0077238 A1 | 3/2012 | Herrema et al. |
| 2012/0077254 A1 | 3/2012 | Morse et al. |
| 2012/0165500 A1 | 6/2012 | Herrema et al. |
| 2012/0202925 A1 | 8/2012 | Srubar et al. |
| 2012/0225476 A1 | 9/2012 | Herrema et al. |
| 2012/0309071 A1 | 12/2012 | Scherson et al. |
| 2013/0005006 A1 | 1/2013 | Herrema et al. |
| 2013/0023674 A1 | 1/2013 | Criddle et al. |
| 2013/0052681 A1 | 2/2013 | Criddle et al. |
| 2013/0071890 A1 | 3/2013 | Criddle et al. |
| 2013/0337516 A1 | 12/2013 | Herrema et al. |
| 2014/0057343 A1 | 2/2014 | Herrema et al. |
| 2014/0206049 A1 | 7/2014 | Herrema et al. |
| 2014/0256026 A1 | 9/2014 | Herrema et al. |
| 2015/0140621 A1 | 5/2015 | Herrema et al. |
| 2015/0247172 A1 | 9/2015 | Herrema |
| 2017/0268026 A1 | 9/2017 | Herrema |
| 2017/0369908 A1 | 12/2017 | Herrema |
| 2018/0119181 A1 | 5/2018 | Herrema et al. |
| 2018/0119182 A1 | 5/2018 | Herrema et al. |
| 2020/0076891 A1 | 3/2020 | Stuart et al. |
| 2020/0115724 A1 | 4/2020 | Herrema |
| 2020/0172942 A1 | 6/2020 | Herrema |
| 2020/0263212 A1 | 8/2020 | Herrema |
| 2020/0347417 A1 | 11/2020 | Herrema |

FOREIGN PATENT DOCUMENTS

| | | |
|---|---|---|
| WO | PCT/US2005/047415 | 12/2005 |
| WO | PCT/US2007/004484 | 2/2007 |
| WO | WO2007/024255 | 3/2007 |
| WO | WO2008/103134 | 8/2008 |
| WO | PCT/US2010/047052 | 8/2010 |
| WO | WO 2011/031566 | 3/2011 |
| WO | PCT/US2012/028210 | 3/2012 |
| WO | WO 2012/122343 | 9/2012 |

OTHER PUBLICATIONS

Bioremediation—field Experience: Field Experience, Paul E. Flathman, Douglas E. Jerger and Jurgen H. Exner, CRC Press, Boca Raton, Florida, 1994, pp. 275-276.

Bothe, Harald, et al. "Heterotrophic bacteria growing in association with Methylococcus capsulatus (Bath) in a single cell production porocess", Applied Microbiology and Biotechnology, Springer, DE vol. 59, No. 1, Jun. 1, 2002 (Jun. 1, 2002), pp. 33-39.

Brigmon, Methanotrophic Bacteria: Use in Bioremediation, Westinghouse Savannah River Company, on-line publication No. WSRC-MS-2001-00058, http://sti.srs.gov/fulltext/ms2001058/ms2001058.html,2001.

Burrows, et al., Substrate Specificites of the Soluble and Particulate Methane Monooxygenases of Methylosinus-Trichosporium OB03B, J. Gen. Microbiol., vol. 130 (12):3327-3333(1984).

Christian et al., Sustainable Biocomposites for Construction, Composites & Polycon 2009, American Composites Manufacturers Association, Jan. 15-17, 2009, Tampa, Florida, pp. 1-6.

Climate Change 2001: Working Group I: The Scientific Basis, Intergovernmental Panel on Climate Change, http://www.grida.no/climate/ipcc_tar/wg1/017.htm, 2001.

Cow Power, htt://www.riverdeep.net/current/2002/03/032502t_cowpower.jhtml, Mar. 2002.

D'Aquino, Rita, "Methane to Protein," Aptagen in the Media, http://www.aptagen.com/corporate/AptagenDocuments/Articles/che.html, Oct. 27, 2000.

Deublein, et al. "Biogas from Waste and Renewable Resources", Part III, Chapter 2.1.1, p. 94. WILEY-VCH Verlag GmbH & Co. KgaA, Weinheim, 2008.

Dias, et al., "Recent Advances in Polyhydroxyalkanoate Production by Mixed Aerobic Cultures: From the Substrate to the Final Product." Macromol. Biosci. (2006) 6, 885-906.

English Translation of Abstract of JP 2003-184575, published Jul. 3, 2003.

Fogel et al., Biodegradation of Chlorinated Ethenes by a Methane-Utilizing Mixed Culture, Applied and Environmental Microbiology, vol. 51(4):720-724 (1986).

Frans-Jaco, et al., "Spatial Distribution and Inhibition by Ammonium of Methane Oxidation in Intertidal Freshwater Marshes" Applied and Environmental Microbiology, (1997) vol. 63(12):4734-4740.

Frigon, et al. "rRNA and Poly-Hydroxybutyrate Dynamics in Bioreactors Subjected to Feast and Famine Cycles" Applied and Environmental Microbiology, Apr. 2006, p. 2322-2330.

Gasser, "Agricultural productivity and the nitrogen cycle," Phil Trans R. Soc Lond. B296;303-314, 1982.

Gay, S.W., "Natural ventilation for freestall dairy barns," Pub. No. 442-763, Virginia Cooperative Extension, Virginia Polytechnic institute and State university, http://www.ext.vt.edu/pubs/bse/442-763/442-763.pdf, 2002.

(56) References Cited

OTHER PUBLICATIONS

Gooch, Curt A., Natural or Tunnel Ventilation of Freestall Structures: What is Right for Your Dairy Facility? www.milkproduct.com, Published Nov. 4, 2005.
Graham, et al. Factors affecting competition between type 1 and type 2 methanotrophs in two organism, continuous-flow reactors. Microb Ecol (1993) vol. 25 p. 1-17.
Helm et al. Characterizing a stable methane-utilizing mixed culture used in the synthesis of a high-quality biopolmer in an open system. Journal of Applied Microbiology, vol. 101, pp. 387-395 (2006).
Helm et al. Potassium deficiency results in accumulation of ultra-high molecular weight poly-beta-hydroxybutyrate in a methane-utilizing mixed culture. Journal of Applied Microbiology, vol. 105, pp. 1054-1061, 2008.
Helm J., Methanotrophic bacteria as producers of poly(beta-hydroxybutyric acid) (PHB)-characterization of the process, the polymer and the stable mixed culture, Tech. Univ. Desden, Faculty of Mechanical Engineering, doctoral thesis (2002).
International Preliminary Report on Patentability of PCT Application No. PCT/US05/47415, dated Feb. 20, 2008.
International Preliminary Report on Patentability of PCT Application No. PCT/US07/04484, dated Sep. 3, 2009.
International Preliminary Report on Patentability of PCT Application No. PCT/US2010/047052, dated Mar. 8, 2012.
International Search Report and Written Opinion of PCT Application No. PCT/US05/47415, dated Aug. 9, 2006.
International Search Report and Written Opinion of PCT Application No. PCT/US07/04484, dated Sep. 26, 2008.
International Search Report for PCT/US2010/047052 dated Dec. 27, 2010.
International Search Report and Written Opinion of PCT Application No. PCT/US2012/028210, dated Aug. 23, 2012.
Jensen, S. et al., "Methanol Improves Methane Uptake in Starved Methanotrophic Microorganisms" Applied and Environmental Microbiology, (1998) vol. 64(3): 1143-1146.
Johnson et al., "Methane emissions from cattle," J. Anim. Sci. 73:2483-2492, 1995.
Lee, et al. "High-density algal photobioreactors using light-emitting diodes" Biotechnology and Bioengineering, vol. 44, Issue 10, pp. 1161-1167 (1994).
Gerlagh, T, Matter 2.0, "A module characterization for the agriculture and food sector" (Jul. 1999). 5.1.1 Enteric fermentation (p. 22). ftp://ftp.ecn.nl/pub/www/library/report/1999/c99048.pdf.
McDonald et al., "The Soluble Methane Monooxygenase Gene Cluster of the Trichloroethylene-Degrading Methanotroph *Methlocystis* sp. Strain M," American Society for Microbiology, 1997, pp. 1898-1904.
Meeting Minutes of Methane to Markets, Agriculture Task Force Meeting dated Jun. 22, 2005. http://www.methanetomarkets.org/resources/ag/docs/ag-meeting.pdf.
Methane Emissions from Livestock Enteric Fermentation (p. 150). Reducing Emissions of Non-CO2 Greenhouse Gases (Sep. 2006). http://www.climatetechnology.gov/stratplan/final/CCTP-StratPlan-Ch07-Sep-2006.pdf.
Müller, et al. "Adaptive responses of Ralstonia eutropha to feast and famine conditions analysed by flow cytometry" J Biotechnol. Oct. 8, 1999;75(2-3):81-97.
Murrell et al., "Regulation of expression of methane monooxygenases by copper ions," Trends in Microbiology 8(5):221-225, 2000.
Nichols, Peter D., and White, D.C., "Accumulation of poly-B-hydroxybutyrate in a methane-enriched, halogenated hydrocarbon-degrading soil column: implications for microbial community structure and nutritional status". Hydrobiologia 1989, 176/177:369-377.
Norferm's future under discussion; Scandinavian Oil-Gas Magazine; http://www.scandoil.com/moxie-bm2/news/company_news/norferms-future-under-dis.shtml, Published Oct. 27, 2005.
Pfluger et al. Selection of Type I and Type II methanotropic proteobacteria in a fluidized bed reactor under non-sterile conditions. Bioresource Technology, vol. 102, pp. 9919-9926, 2011 (available online Aug. 19, 2011).

Pieja et al., Distribution and Selection of Poly-3-Hydroxybutyrate Production Capacity in Methanotrophic Proteobacteria, Microb Ecol (2011), vol. 62, pp. 564-573.
Pieja et al., Poly-3-Hydroxybutyrate Metabolism in the Type II Methanotroph Methylocystis parvus OBBP, Applied and Environmental Microbiology, Sep. 2011, vol. 77(17), p. 6012-6019.
Polakovic, "Getting the Cows to Cool It," Los Angeles Times, Jun. 7, 2003, pp. A1 and A17, Los Angeles, CA U.S.A.
Reddy, et al., Polyhydroxyalkanoates: An Overview, Bioresource Technology, vol. 87: 137-146 (2003).
Reis, et al. "Production of polyhydroxyalkanoates by mixed microbial cultures" Bioprocess and Biosystems Engineering, vol. 25, No. 6, 377-385, DOI: 10.1007/s00449-003-0322-4 (2003).
Singh et al. "Bacillus subtllis as potential producer for polyhydroxyalkanoates"; Microbial Cell Fractories; Jul. 20, 2009, vol. 8, No. 38; p. 1-11.
Shah, et al. "Batch Cultivation of Methylosinus trichosporium OB3b: V. Characterization of Poly-B-Hydroxybutyrate Production Under Methane-Dependent Growth Conditions" Biotechnology and Bioengineering, vol. 49, pp. 161-171 (1996).
Stanley, et al., Copper stress underlies the fundamental change in intracellular location of methane mono-oxygenase in methane-oxidizing organisms: Studies in batch and continuous cultures., Biotech Letters, vol. 5(7):487-492 (1983).
Jolley, Ainsley, Technologies for Reducing Non-Energy-Related Emissions (Mar. 2006). Enteric Fermentation (p. 8). http://www.cfses.com/documents/climate/10_%20Jolley_Technologies_for_Reducing_Non-energy_Related_Emissions.pdf.
Tellez, et al., Isolation of copper biochelates from Methylosinus trichosporium 0B3b and soluble methane monooxygenase mutants, App. And Env. Microbiol., vol. 64(3):1115-1122 (1998).
Eckard, Richard, "The abatement challenge for Australian Agriculture" Greenhouse in Agriculture, The University of Melbourne and Department of Primary Industries, Victori (2007). Enteric methane (p. 2). http://www.dpc.vic.gov.au/CA256D800027B102/Lookup/Forum1EckardPaper/$file/Eckard%2017%20August%202007%20-%20The%20abatement%20challenge%20for%20agriculture.pdf.
Tyson, John T. et al., Tunnel Ventilation for Tie Stall Dairy Barns, Penn State, College of Agricultural Sciences, Agricultural and Biological Engineering, 2nd Edition Jan. 1, 2004.
Verlinden, et al., "Bacterial synthesis of biodegradable polyhydroxalkanoates," Journal of Applied Microbiology, 102 (2007), p. 1437-1449.
Wendlandt et al. The potential of methane-oxidizing bacteria for applications in environmental bitechnolgy. Engineering in Life Sciences, vol. 10, pp. 87-102 (2010).
Wendlandt et al., "Possibilities for controlling a PHB accumulation process using various analytical methods," J. of Biotechn. 2005, vol. 117, pp. 119-129.
Wendlandt et al., "Producing poly-3-hydroxybutyrate with a high molecular mass from methane," J. Biotechnol. 2001, vol. 86, pp. 127-133, see pp. 127-128.
Zhang et al. Biosynthesis of poly-3-hydroxybutyrate with a high molecular weight by methanotroph from methane and methanol. Joural of Natural Gas Chemistry, vol. 17, pp. 103-109 (2008).
Bourne et al. "Comparison of pmoA PCR Primer Sets as Tools for Investigating Methanotroph Diversity in Three Danish Soils", Applied and Environmental Microbiology, Sep. 2001. p. 3802-3809.
Henrysson et al., "Influence of the endogenous storage lipid poly-β-hydroxybutyrate on the reducing power availability during cometabolism of trichloroethylene and naphthalene by resting methanotrophic mixed cultures," Applied and Environmental Microbiology 59(5): 1602-1606, 1993. (Year: 1993).
International Search Report and Written Opinion, for International Application No. PCT/US2020/036986, dated Aug. 26, 2020, in 15 pages.
Madden et al., "Introducing the Carbor Impact Factor", thejei.com. Jan. 31, 2016, http://www.thejei.com/introducing-the-carbon-impact-factor/.
Sherry, "How Blockchain Can Make Carbon Markets More Accessible"., ecosystemmarketplace.com, Oct. 2, 2018, https://www.ecosystemmarketplace.com/articles/how-blockchain-can-make-carbon-markets-more-accessible//.

(56) References Cited

OTHER PUBLICATIONS

U.S. Appl. No. 10/687,272 (U.S. Pat. No. 6,982,161), filed Oct. 15, 2003, Process for the Utilization of Ruminant Animal Methane Emissions.
U.S. Appl. No. 11/208,808 (U.S. Pat. No. 7,745,197), filed Aug. 22, 2005, Process for the Utilization of Ruminant Animal Methane Emissions.
U.S. Appl. No. 12/825,277 (U.S. Pat. No. 8,177,870), filed Jun. 28, 2010, Process for the Utilization of Ruminant Animal Methane Emissions.
U.S. Appl. No. 13/458,772 (U.S. Pat. No. 8,465,876), filed Apr. 20, 2012, Systems for the Utilization of Ruminant Animal Methane Emssions.
U.S. Appl. No. 13/918,395 (U.S. Pat. No. 8,945,915), filed Jun. 14, 2013, Energy Production Systems Utilizing Ruminant Animal Methane Emissions.
U.S. Appl. No. 11/676,928 (U.S. Pat. No. 7,579,176), filed Feb. 20, 2007, Method for the Production of Polyhydroxyalkanoic Acid.
U.S. Appl. No. 12/064,603 (U.S. Pat. No. 8,071,342), filed Feb. 22, 2008, Process for the Treatment of Substrate-Variable Methane Emissions.
U.S. Appl. No. 13/310,542 (U.S. Pat. No. 8,735,113), filed Dec. 2, 2008, Methods and Systems for Production of Polyhydroxyalkanoate.
U.S. Appl. No. 13/609,151 (U.S. Pat. No. 8,703,470), filed Sep. 10, 2012, Method for Producing Polyhydroxyalkanoic Acid.
U.S. Appl. No. 14/286,274, filed May 23, 2014, Biological Compositions for the Production of Functionally Consistent Products.
U.S. Appl. No. 14/526,228 (U.S. Pat. No. 9,850,508), filed Oct. 28, 2014, Polyhydroxyalkanoate Production Methods and Systems for Same.
U.S. Appl. No. 14/990,713 (U.S. Pat. No. 9,868,967), filed Jan. 7, 2016, Polyhydroxyalkanoic Acid Compositions and Methods for Generating Same.
U.S. Appl. No. 15/849,193, filed Dec. 20, 2017, Polyhydroxyalkanoate Production Methods and Systems for Same.
U.S. Appl. No. 15/849,531 (U.S. Pat. No. 10,494,652), filed Dec. 20, 2017, Polyhydroxyalkanoic Acid Compositions and Methods for Generating Same.
U.S. Appl. No. 16/671,030, filed Oct. 31, 2019, Polyhydroxyalkanoic Acid Compositions and Methods for Generating Same.
U.S. Appl. No. 12/546,138 (U.S. Pat. No. 8,263,373), filed Aug. 24, 2009, Method for Producing Polyhydroxyalkanoic Acid.
U.S. Appl. No. 13/392,502, filed Feb. 24, 2012, Process for the Production of Polyhydroxyalkanoates.
U.S. Appl. No. 14/466,388, filed Aug. 22, 2014, Polyhydroxyalkanoate Production and Related Processes.
U.S. Appl. No. 14/003,751 (U.S. Pat. No. 9,040,267), filed Sep. 6, 2013, Polyhydroxyalkanoate Production Method.
U.S. Appl. No. 14/698,670, filed Apr. 28, 2015, Polyhydroxyalkanoate Production Method.
U.S. Appl. No. 13/802,622 (U.S. Pat. No. 9,085,784), filed Mar. 13, 2013, Polyhydroxyalkanoate Production Methods and Materials and Microorganisms Used in Same.
U.S. Appl. No. 14/740,056, filed Jun. 15, 2015, Polyhydroxyalkanoate Production Methods and Materials and Microorganisms Used in Same.
U.S. Appl. No. 15/643,905, filed Jul. 7, 2017, Polyhydroxyalkanoate Production Methods and Materials and Microorganisms Used in Same.
U.S. Appl. No. 16/577,373, filed Sep. 20, 2019, Polyhydroxyalkanoate Production Methods and Materials and Microorganisms Used in Same.
U.S. Appl. No. 15/182,542, filed Jun. 14, 2016, Systems and Methods for Calculating, Apportioning and Distributing Carbon Credits.
Nori, "A blockchain-based marketplace for removing carbon dioxide from the atmosphere," Version 3.0, Aug. 27, 2018.

* cited by examiner

POLYHYDROXYALKANOATE PRODUCTION METHODS AND SYSTEMS FOR SAME

RELATED APPLICATIONS

This application is a continuation of co-pending U.S. patent application Ser. No. 15/849,193, filed on Dec. 20, 2017, which is a continuation of U.S. patent application Ser. No. 14/526,228, filed on Oct. 28, 2014, now U.S. Pat. No. 9,850,508, which is a continuation of U.S. patent application Ser. No. 14/286,274, filed May 23, 2014, which is a continuation of U.S. patent application Ser. No. 13/310,542, filed Dec. 2, 2011, now issued as U.S. Pat. No. 8,735,113, the entire disclosures of each of which is incorporated by reference herein.

BACKGROUND

Field Of Invention

Several embodiments of the invention relate generally to a system and methods for the treatment of methane emissions, and in several embodiments, to systems and/or methods for the treatment of methane emissions through the use of methanotrophic microorganisms.

Description of the Related Art

Methane emissions, or methane off-gases, are generated by a variety of natural and human-influenced processes, including anaerobic decomposition in solid waste landfills, enteric fermentation in ruminant animals, organic solids decomposition in digesters and wastewater treatment operations, and methane leakage in fossil fuel recovery, transport, and processing systems. As a particularly potent greenhouse gas, methane emissions are estimated to be responsible for about twenty percent of anthropogenic global warming, and thus represent a significant environmental problem. Accordingly, there have been numerous efforts in the past to remediate, control, and/or otherwise treat methane emissions from a variety of sources.

SUMMARY

Several embodiments disclosed herein are directed to processing methane that is emitted from landfills, coal mines, wastewater treatment plants, manure digesters, agricultural digesters, compost heaps, enclosed agricultural feedlots, and leaking or otherwise emitting petroleum systems.

Atmospheric methane emissions are estimated to account for about twenty percent of global warming. In addition to the environmentally destructive effect of methane emissions, such emissions represent wasted carbon and energy, as methane could theoretically be used to generate energy (e.g., heat homes or drive combustion-based processes), provide fuel, and, or serve as a carbon input for the generation of useful products, such as chemicals, plastics, fuels, and other products.

Several methods are known for the treatment of natural and human-influenced methane emissions. Used in conjunction with methane emissions collection methods, such as landfill gas extraction wells/blowers and coal mine methane ventilation systems, the treatment of air containing captured methane emissions includes the use of turbines, microturbines, engines, reverse-flow reactors, fuel cells, and boilers to convert methane emissions into heat and/or electricity. Other methods for the treatment of methane emissions include the conversion of methane emissions into pipeline-quality, liquefied, or compressed natural gas.

The utilization of methane emissions for the production of fuel, heat, and/or electricity is described by a number of patents, including U.S. Pat. Nos. 5,642,630, 5,727,903, 5,842,357, 6,205,704, 6,446,385, and 6,666,027, each of which is herein incorporated by reference in its entirety. U.S. Pat. No. 5,642,630 describes the use of landfill gas to produce high quality liquefied natural gas, liquefied carbon dioxide, and compressed natural gas products. U.S. Pat. No. 5,727,903 describes the use of landfill gas to create vehicle grade fuel. U.S. Pat. No. 5,842,357 describes the use of landfill gas to create high grade fuel and food-grade carbon dioxide. U.S. Pat. Nos. 6,205,704 and 6,446,385 describe the use of landfill gas to provide heat, electricity, and/or carbon dioxide to enhance greenhouse operations. U.S. Pat. No. 6,666,027 describes the use of off-gas from landfills and digesters to power turbines for electricity generation.

Although each of these methods can treat methane emissions under certain specific conditions, none are known to be economically and/or technologically feasible in most practical contexts, including under a range of sub-optimal methane-in-air conditions. For example, the effectiveness of such methods is reduced or eliminated entirely under conditions where the flow rate, concentration, or purity of methane gas emissions is variable (e.g., unpredictable, low, and/or otherwise unfavorable), as is commonly the case when using natural sources of methane emissions or when considering methane emissions from sources such as landfills, dairy operations, wastewater treatment plants, or industrial off-gases.

Methane-utilizing, or methanotrophic, microorganisms are known in the microbiology art for their capacity to grow and reproduce using methane as a source of carbon and/or energy. These microorganisms are known to grow in a wide range of diverse methane availability conditions. Accordingly, methanotrophic microorganisms have been proposed in the past as a potential tool for the remediation of methane emissions, particularly in conditions where other treatment methods are technologically and/or economically unfeasible.

Two methods have been proposed for the utilization of methanotrophic microorganisms to treat methane emissions. In one proposed process, methanotrophic microorganisms are naturally present or purposefully situated in high-methane emissions environments, such as landfill covers or coal mines. The methanotrophic microorganisms are provided with growth-stimulating nutrients, such as oxygen, water, or mineral salts, to encourage increased microbial methane emission uptake rates. This method may be carried out using nutrient injection methods such as air or water sparging to induce increased methanotrophic growth and oxidation rates in high emissions environments. U.S. Pat. No. 6,749,368, for example, describes methanotrophic microorganisms that are placed in an aerated soil cover above a municipal landfill in order to oxidize and reduce methane emissions.

In a second proposed process, air containing methane emissions is diverted into an environment containing methanotrophic microorganisms in order to cause the microbial breakdown of methane emissions. This method may be carried out by diverting air containing methane emissions into a biofiltration column containing methanotrophic microorganisms, water, and a microorganism growth medium, whereby electricity, water, nitrogen, trace minerals, and other materials are continuously added to and consumed by the system in order to effect the microbial breakdown of methane emissions.

Both of these methanotrophic treatment techniques cannot effectively or efficiently reduce methane emissions. Indeed, the application of these processes has been almost entirely precluded in practice because both have continuous requirements for costly materials, such as electricity and minerals, yet neither generates economic benefits to recover those capital costs of methane emission treatment. Thus, the use of methanotrophic microorganisms for the treatment of methane emissions which generate no commercially useful products is simply too costly to operate and sustain over time. Prior to the Applicants' discovery, no methods were known to enable the treatment of methane emissions wherein commercially useful (e.g., high value and having consistent functional properties) products could be generated, and, accordingly, the utilization of methanotrophic microorganisms for the treatment of methane emissions has been precluded in practice.

Accordingly, there exists a significant need to develop methods and systems that enable methanotrophic methane emissions treatment to be carried out in a manner that generates commercially useful (e.g., high value and having consistent functional properties) products, thereby rendering the process commercially viable and technologically, financially, and logistically sustainable.

Several embodiments of the present invention address the need for a system that enables biological methane emissions treatment to generate harvestable, e.g., commercially useful, products, and thus be technologically, financially, and logistically sustainable and viable. Prior to embodiments of Applicants' invention as disclosed herein, gaseous emissions comprising methane have never been used in conjunction with methanotrophic microorganisms to reduce the environmentally destructive impact of methane emissions while simultaneously creating a harvestable product (or products) from that methane.

In several embodiments, the gaseous emissions (which comprise some amount of methane) from landfills, coal mines, agricultural sites, or petroleum sites are captured and conveyed to a bioreactor containing methanotrophic microorganisms. In some embodiments, the gaseous emissions do not need to undergo substantial purification. In still additional embodiments, no purification of the gaseous emissions is required, though in other embodiments, purification is optionally performed. The microorganisms use the methane as a source of carbon or energy and, in some embodiments, produce useful end-products, such as polymers or plastics, with physical, chemical, and performance qualities that can used for commercial purposes, e.g., to replace oil-based plastics. The polymers or plastics can then be used to synthesize various types of materials, including, but not limited to, biodegradable plastic parts. In some embodiments, the polymers can be used to replace a wide range of oil-based plastics, such as polypropylene, polyethylene, and polystyrene, due to the physical properties of the plastics, which are also biodegradable. Thus, some preferred embodiments of the invention offer a tremendous benefit to the environment in at least two ways: first, methane emissions are substantially reduced on the front end, thereby sequestering carbon that would have otherwise been emitted into the air, and second, a biodegradable polymer that can be used to replace oil-based plastic is produced in useful quantities as the end-product, thereby reducing the use of non-renewable oil.

The term "gaseous emission" as used herein shall be given its ordinary meaning and shall also refer to off-gases and/or gases produced, generated, or emitted by natural and/or human-influenced processes, including anaerobic decomposition in solid waste landfills, organic decomposition in digesters and wastewater treatment operations, agricultural sites, and in fossil fuel recovery, transport, distribution, delivery, and processing systems.

Although the prior art recognized that methanotrophic organisms could use methane to produce polymers, the prior art did not disclose, teach, or suggest an effective method by which destructive gaseous emissions that comprise methane could be used to produce polymers (or other harvestable and useful products as disclosed herein) from gas streams comprising methane and non-methane compounds or substances that impact the metabolism of methanotrophic microorganisms, as the case may be the case with industrial or municipal methane emissions. Prior to Applicants' invention, the production of commercially useful polymers (or other products) by methanotrophic organisms from non-pure methane emissions from sources such as, e.g., landfill gas, was not feasible, because the process would generate polymers or proteins (or other biological products such as those disclosed herein) having a wide, inconsistent, and unpredictable range of functional properties based on the varied type and varied concentration of non-methane impurities contained in the methane emissions streams (as well as the variation in the concentration of methane itself). In contrast, several embodiments of the present invention do not require artificial laboratory grade methane (which is essentially pure methane) to produce harvestable/commercially useful polymers. Instead, environmentally destructive gases that are already present in the environment, particularly those gases comprising variable concentrations of methane and non-methane compounds or substances that impact methanotrophic metabolism, are used as the source of methane.

Therefore, in several embodiments there are provided methods for producing a polyhydroxyalkanoate (PHA) in a culture of methanotrophic microorganisms, comprising providing a gas comprising methane and one or more non-methane substances, providing a culture of methanotrophic microorganisms and a microorganism culture medium comprising at least a first essential nutrient and a second essential nutrient, exposing the culture to the gas, and controlling the concentration of the first essential nutrient in the culture medium to a concentration sufficient to induce the methanotrophic microorganisms to produce particulate methane monooxygenase (pMMO) and/or soluble methane monooxygenase (sMMO), and controlling the concentration of the second essential nutrient, wherein the control of the second essential nutrient causes the methanotrophic microorganisms to produce the PHA.

In addition to the methods disclosed herein, there is also provided a system for producing PHAs with consistent functional properties from a culture of methanotrophic microorganisms. In several embodiments, the system comprises a culture of methanotrophic microorganisms capable of metabolizing gas comprising methane and one or more non-methane substances, a microorganism culture medium comprising at least a first essential nutrient and at least a second essential nutrient, a bioreactor for culturing the methanotrophic microorganisms in the presence of the microorganism culture medium, and a conveyer that conveys the gas from the source of gas into the bioreactor, thereby exposing the methanotrophic microorganisms and the microorganism culture medium to the gas. In several embodiments, the concentration of the first essential nutrient is controlled to a concentration sufficient to induce the methanotrophic microorganisms to produce particulate methane monooxygenase (pMMO) and/or soluble methane monooxygenase (sMMO) and the concentration of the essential nutrient is controlled to a concentration sufficient to cause the methanotrophic microorganisms to generate PHA. In several embodiments, the control of the concentration of the first essential nutrient and the second essential nutrient make up a production cycle comprising methane monooxygenase production followed by PHA production. In several embodiments, the system is configured to repeat the production cycle to induce at least a first production cycle and a second production cycle, wherein the functional properties of PHA generated in the first production cycle are substantially similar to the functional properties of PHA generated in the second production cycle.

In several embodiments, the PHA is selected from the group consisting of polyhydroxybutyrate, polyhydroxybutyrate-covalerate (PHBV), poly-4-hydroxybutyrate (P4HB), polyhydroxyhexanoate (PHHx), and polyhydroxyoctanoate (PHO).

In several embodiments, certain individual steps or combinations of steps can be categorized based on the result achieved after performance of those steps. For example, in certain embodiments, the method comprises a microorganism growth phase, a monooxygenase production phase, and PHA production phase. Additional embodiments comprise, for example, a harvesting phase. In some embodiments, or more steps can be performed a single time or, in other embodiments, can be repeated multiple times. For example, in some embodiments induction of pMMO or sMMO production is followed by induction of PHA production, which comprises a production cycle. In several embodiments, multiple production cycles are performed (e.g., induction of pMMO or sMMO production followed by induction of PHA production multiple times), thereby resulting in at least a first production cycle and a second production cycle. The repeated performance of such production cycles allows the enhanced production of PHA (e.g., greater concentrations and/or more similar functional properties). In some embodiments the repetition of such production cycles increases the overall efficiency of the process (e.g., a greater percentage of the methane from the gas is converted to useful and harvestable and product such as PHA).

Consistency in the characteristics of a manufactured product are generally desirable, in that a user of such a product can expect that the behavior of the product will be similar from use to use (e.g., from batch to batch). This consistency reduces inefficiencies in using the product because a more standardized protocol for use of the product can be developed and implemented. Moreover, consistency increases the user's ability to obtain reproducible results over time (e.g., a product subsequently produced by the user is likely to also be more consistent over time). The methods and systems disclosed herein are advantageous in that they allow the production of products that are have consistent functional properties, even in spite of microbial growth conditions that may vary substantially over time. In several embodiments, polymers are produced using the methods and/or systems disclosed herein. In some embodiments, the functional characteristics of the generated polymers include, but are not limited to molecular weight, polydispersity and/or polydispersity index, melt flow and/or melt index, monomer composition, co-polymer structure, melt index, non-PHA material concentration, purity, impact strength, density, specific viscosity, viscosity resistance, acid resistance, mechanical shear strength, flexular modulus, elongation at break, freeze-thaw stability, processing conditions tolerance, shelf-life/stability, hygroscopicity, and color. In several embodiments, consistency in more than one of these functional properties is achieved. For example, in some embodiments, consistent molecular weight, polydispersity, and combinations thereof are achieved.

The generation of a product, such as PHA, that has consistent functional characteristics enables the end user of the PHA to have greater assurance that the PHA will perform in a similar fashion each time it is used, which reduces inefficiencies in manufacturing or other process that utilize that PHA and also may increase the quality, performance, and/or value of a subsequently produced item.

In several embodiments, the molecular weight of the PHA produced in a first production cycle differs from the molecular weight of the PHA produced in a subsequent production cycle by less than 50%. In additional embodiments, the molecular weight of PHA produced in different production cycles differs by 25% or less, 20% or less, 10% or less, 5% or less, or 1% or less. In several embodiments, the molecular weight of PHA produced ranges from about 100 to about 5,000,000 Daltons. In several embodiments, the molecular weight of PHA produced ranges from about 100,000 to about 2,500,000 Daltons. Other molecular weight ranges are achieved in certain other embodiments.

In several embodiments, the polydispersity of the PHA produced in a first production cycle differs from the polydispersity of the PHA produced in a subsequent production cycle by less than about 75%. In some embodiments, the polydispersity of the PHA produced in various production cycles differs by less than about 50%. In some embodiments, the polydispersity between production cycles differs by about 25% or less, about 20% or less, about 10% or less, about 5% or less, or about 1% or less. In some embodiments the polydispersity of PHA produced in a first production cycle is indistinguishable from that of PHA produced in different production cycle. In several embodiments, the polydispersity ranges from about 0.1 to about 5.0, including about 0.1 to about 0.5, about 0.5 to about 1.0, about 1.0 to about 1.5, about 1.5 to about 2.0, about 2.0 to about 2.5, about 2.5 to about 3.0, about 3.0 to about 3.5, about 3.5 to about 4.0, about 4.0 to about 4.5, about 4.5 to about 5.0, and overlapping ranges thereof.

In several embodiments, the concentration of the pMMO and the sMMO produced in the microorganisms in a first production cycle differs by less than about 75% from the total concentration of the pMMO and the sMMO produced in the microorganisms in a subsequent production cycle. In additional embodiments, concentration of the pMMO and the sMMO produced in a first production cycle differs from the concentration produced in a different production cycle by less than about 50%, by less than about 25%, by less than about 10%, or by less than about 1%.

In several embodiments, the one or more non-methane substances have the ability to impact the metabolism of the methanotrophic microorganisms. Advantageously, however, the method allows the production of PHA having consistent functional properties despite the potential impact that such substances have on the metabolism of the microorganisms. In several embodiments, the one or more non-methane substances are selected from the group consisting of methanol, acetone, acetate, formate, formaldehyde, hydroxyalkanoates, hydroxybutyrate, octanoic acid, octanol, carbon dioxide, nitrogen, oxygen, di-oxygen, di-nitrogen, water, water vapor, argon, ethane, propane, butyrate, butyric acid, hexanoic acid, hexanol, heptanoic acid, heptanol, pentane, pentanoic acid, and volatile organic compounds.

In several embodiments, the culture comprises two or more species of methanotrophic microorganisms. In several embodiments, the two or more species are selected based on complementary characteristics. For example, a first species may be selected based on its ability to metabolize low concentrations of methane while a second species may be selected based on its ability to maintain metabolic functionality in the face of impurities in the culture environment. In some embodiments, by placing culturing two such species together a more efficient processing of a gas comprising methane and one or more non-methane compounds (such as, for example landfill gas or gas from decomposition in digesters and wastewater treatment operations) is achieved.

At least in part, the control of the concentration of essential nutrients in the culture media allows the metabolic synchronization of the microorganisms within the culture such that functionally consistent products are generated. In several embodiments, the first and the second essential nutrients comprise one or more of carbon, hydrogen, nitrogen, oxygen, phosphorus, potassium, calcium, sodium, chlorine, methane, carbon dioxide, magnesium, iron, copper, sulfate, manganese, boron, zinc, aluminum, nickel, chromium, cobalt, or molybdenum.

In some embodiments, combinations of essential nutrients are controlled. In some embodiments, controlling of the first essential nutrient or of the second essential nutrient comprises increasing the concentration of first essential nutrient or of the second essential nutrient. In some embodiments, the controlling of the first essential nutrient or of the second essential nutrient comprises decreasing the concentration of first essential nutrient or of the second essential nutrient. In some embodiments, the first and second essential nutrients are the same nutrient.

In still additional embodiments, a first essential nutrient may be increased while a second essential nutrient may be decreased. In certain embodiments, controlling the concentration comprises maintaining the concentration within a certain range (as opposed to increasing or decreasing the concentration of that nutrient). In such embodiments, maintenance may be achieved by adding sufficient amounts of that nutrient to offset consumption (e.g., metabolism) of the nutrient by the methanotrophic microorganisms. Likewise, the overall volume of the culture media can be adjusted, for example by adding or removing water, such that the concentration of a particular nutrient is maintained. In some embodiments, maintenance of the concentration of essential nutrient comprises limiting variation in the concentration to less than about 50%. In some embodiments, the variation is limited to less than about 25%, less than about 20%, less than about 15%, less than about 10%, or less than about 5%. Depending on the nutrient, in some embodiments greater or lesser degrees of variation are allowable.

Moreover, several embodiments of the present invention are particularly advantageous because gaseous emissions comprising low concentrations of methane can be used, rather than pure (high methane concentration, for example, concentrated methane and/or methane with low or non-existent contaminants) methane. Although certain turbine systems are capable of converting gaseous emissions into energy, the concentration of methane must be high. Likewise, although certain fuel cells can use methane in low concentrations, gaseous emissions such as those employed in the methods disclosed herein cannot be used because the fuel cells require methane that must be substantially pure.

Advantageously, in several embodiments, gaseous emissions comprising methane in a concentration of less than about 95%, less than about 80%, less than about 70%, less than about 60%, less than about 50%, less than about 40%, less than about 30%, less than about 20%, less than about 10%, less than about 5%, and less than about 1% can be used. Thus, several embodiments of the present invention are particularly useful for older landfills, which may produce methane emissions with methane concentrations of about 0.1% to less than about 20% of total gaseous emissions as they age. Likewise, several embodiments of the present invention are particularly useful for coal mines, which may produce methane in concentrations of less than about 5% of total gaseous emissions, and in some cases about 1% methane. Thus, without the benefit of certain preferred embodiments of Applicants' invention, these sources of methane (and other gases) pollution—which alone produce methane as a small part of their total gaseous emissions—cumulatively contribute significantly to the total amount of methane in the environment and thus ultimately to the greenhouse effect.

As discussed previously, methane emissions are an environmentally-destructive material and represent a largely unusable source of energy and carbon. In several embodiments of the invention, methane emissions are used to produce a useful end-product (or products) that can be used or sold for use, thereby providing an economic incentive to a methane emissions reduction effort. While in several embodiments, the harvestable and useful end-product is a polymer (e.g., PHA), additional harvestable goods include, but are not limited to, the microorganism culture itself, products or compositions that can be obtained from the microorganism culture (e.g., a harvested enzyme, such as methane monooxygenase, including particulate methane monooxygenase and/or soluble methane monooxygenase), the oxidative products of methane monooxygenase, methanol, carbon dioxide, or combinations thereof. Thus, in some embodiments, gaseous emissions comprising methane are used to grow a microorganism culture to a density and quality that is capable of being harvested and commercially used, sold, or traded. In one embodiment, the microorganism culture and/or the products created thereby can be used, for example, as a nutrition source for livestock, exhibiting a consistent polymer functional profile, or a biodegradable plastic exhibiting commercially useful properties, such as consistent molecular weight and consistent molecular composition. In some embodiments, the end-product is a culture of microorganisms, or the products generated by those microorganisms (e.g., PHA thermoplastic polymers), or combinations thereof.

In several embodiments of the invention, methane emissions are processed to produce useful and harvestable products. These products include, but are not limited to: protein-rich or polymer-rich biomass, polyhydroxyalkanoate (PHA), polyhydroxybutyrate (PHB), polyhydroxybutyrate-valerate (PHB/V), particulate or soluble methane monooxygenase (pMMO or sMMO, respectively), vaccine derivatives, enzymes, polymers, cellular materials, formaldehyde, and methanol, propylene oxide, or combinations thereof. In several embodiments of the invention, methanotrophic microorganisms can be manipulated and processed to generate useful (e.g., defined, consistent, and harvestable) goods in sterile, semi-sterile, and/or non-sterile conditions.

In several embodiments of the invention, a culture of suitable methanotrophic microorganisms is provided for the efficient, effective, and commercially viable treatment of methane emissions. The prior art generally criticizes the use of methanotrophic organisms to treat methane emissions because, as described above, such a process was thought to generate an varied and unpredictable, inefficient, and unreliable culture of microorganisms and/or products. For example, the prior art teaches that bioremediation and biofiltration generates a microorganism conglomerate that is non-specific, non-defined, and/or highly variable over time according to shifts in nutrient availability, air contamination, species interaction, and so on. As emphasized in U.S. Pat. No. 6,599,423, "prior art teaches that ex situ biofilters and bioreactors are akin to microorganism zoos, with the microorganism cultures naturally adapting, dominating, and maintaining themselves according the various compounds, food sources, and contaminants present or fed to the biodegradation media . . . changes, adaptations, and dominance of certain cultures will occur even in such isolated and inoculated cultures after operation begins and the biofilters or bioreactors are subjected to complex mixtures of food sources, contaminants, and microorganisms present in the natural environment."

As discussed above, such changes that occur in the culture over time can lead to corresponding changes in the products that are harvested from the culture. Absent methods of control, as disclosed herein, microbial cultures and the byproducts generated from the growth thereof are created in a variable, non-specific, unpredictable, speculative, or otherwise non-useful manner. Product variability is generally undesired, and by contrast, in several embodiments of the present invention, systems for using and methods of using microorganisms in a highly controlled manner for the treatment of gaseous emissions are provided. In one embodiment, the invention provides a mechanism to cause a culture of methanotrophic microorganisms to produce a stable or controlled metabolic end-product (e.g., PHA) despite variability in concentrations of different methanotrophic microorganism species, or metabolic adaptations amongst the methanotrophic microorganisms in the culture as culture medium conditions change. Specifically, in one embodiment, the invention enables the controlled and stable production of PHA polymers by methanotrophic microorganisms in a culture medium despite changes in the culture and/or culture medium caused by the presence of non-methane compounds or substances that influence the metabolism by methanotrophic microorganisms. Specifically, by controlling the production of sMMO or pMMO in the methanotrophic microorganism culture, the metabolic status of the culture and/or the sources of carbon that may be metabolized by the culture are controlled, which enables the simultaneous (or subsequent) induction of PHA polymer synthesis by the methanotrophic microorganisms.

In several embodiments of the invention, an apparatus or system for processing methane emissions and producing harvestable products is provided. In one embodiment, the system comprises (i) a source of gaseous emissions, wherein the gaseous emissions comprise methane and at least one non-methane compound, (ii) methanotrophic microorganisms that use methane as a source of carbon or energy, (iii) a bioreactor that encloses or contains the methanotrophic microorganisms, and (iv) a conveyer that conveys the gaseous emissions into the bioreactor, thereby exposing the methanotrophic microorganisms to the gaseous emissions and causing the methanotrophic microorganisms to produce a harvestable product after using the methane as a source of carbon or energy, wherein the conditions within the bioreactor are controlled to enable the production of one or more harvestable products.

In accordance with several embodiments of the invention, a novel method for enabling the viable treatment of air containing methane emissions is provided. In one embodiment, methanotrophic microorganisms and air containing methane emissions are mutually-exposed to cause or enable harvestable (e.g., commercially useful) product formation. The harvestable product may be used or sold. In additional embodiments of the invention, air containing methane emissions may be used to create single cell protein, enzymes, polymers, or other bio-based products in a manner that enables harvest of commercially useful product. In still further embodiments, more than one of the harvestable products disclosed herein are produced together (e.g., sequentially or simultaneously).

In some embodiments, the invention comprises a method of processing methane emissions for the production of a harvestable product, comprising: providing a gaseous emission comprising methane and providing methanotrophic microorganisms, exposing the methanotrophic microorganisms to the gaseous emission, wherein the methanotrophic microorganisms use at least a portion of the methane as a source of carbon or energy, and controlling the concentration of copper and one or more essential nutrient, such as nitrogen, oxygen, magnesium, phosphorus, calcium, sodium, sulfate, methane, carbon dioxide, iron, manganese, zinc, cobalt, chromium, aluminum, boron, and/or molybdenum, wherein the methanotrophic microorganisms produce a harvestable (e.g., commercially useful, functional, defined, and/or consistent) product after using the methane as a source of carbon or energy.

In several embodiments, the harvestable product comprises a polymer (such as polyhydroxyalkanoate (PHA), polyhydroxybutyrate (PHB), and polyhydroxybutyrate-valerate (PHB/V)). In another embodiment, the harvestable product comprises one or more of the following: microorganism biomass, methane monooxygenase (particulate or soluble), protein-rich biomass, enzymes, and cellular contents. In additional embodiments, the harvestable product comprises a quantifiable reduction in methane emissions. In still further embodiments, the methods and systems disclosed herein result in combinations of one or more of the harvestable products disclosed herein.

In several embodiments, the gaseous emission comprises a gas selected from the group consisting of one or more of the following: carbon dioxide, ammonia, nitrous oxide, air, nitrogen, and ozone. In one embodiment, the gaseous emission comprises unpurified landfill gas, partially purified landfill gas, anaerobically-generated gas, natural gas, or gas from the production, generation, distribution, and/or processing of fossil fuels. In one embodiment, one or more impurities are removed from the gaseous emission. In another embodiment, the gaseous emission is disinfected using ultraviolet light. In several embodiments, multiple sources of gaseous emissions are used (e.g., the gaseous emissions are combined).

In one embodiment, the invention comprises harvesting the harvestable product for commercial or industrial sale or use.

In one embodiment, the invention comprises substantially reducing or eliminating (or otherwise adjusting, controlling, or depleting) the concentration of nitrogen available to the methanotrophic microorganisms. In some embodiments, other elements, nutrients, or compounds that are available to the methanotrophic microorganisms are reduced, substantially reduced, depleted, eliminated, or otherwise adjusted or controlled (in addition to or in place of the nitrogen) in order to induce product formation. Such elements and compounds include, but are not limited to carbon, oxygen, magnesium, phosphorus, phosphate, potassium, sulfate, sulfur, calcium, boron, aluminum, chromium, cobalt, iron, copper, nickel, manganese, molybdenum, sodium, nitrogen, nitrate, ammonia, ammonium, urea, amino acids, methane, carbon dioxide, and/or hydrogen.

In several embodiments, the invention comprises using gaseous emissions having methane concentrations in the range of about 0.1% to about 10%, in the range of about 10% to about 20%, and at concentrations greater than about 20%. In another embodiment, the methane concentration is less than about 5%. In yet another embodiment, the methane concentration is between about 30% to about 60% of the total gaseous emissions, and carbon dioxide concentration is about 30% to about 60%. The latter numbers are typical of certain landfill emissions.

In several embodiments, the gaseous emission is generated by one or more of the following: coal mine, wastewater treatment operation, agricultural digester, enclosed feedlot, petroleum transport system, and petroleum recovery system.

In several embodiments, the microorganisms comprise naturally-occurring or genetically-modified microorganisms, or a combination thereof, that use methane as a source of carbon or energy for growth or reproduction. The methanotrophic microorganisms may include one or more of the following: *Methylococcus capsulatus, Alcaligenes acidovorans, Bacillus firmus,* and *Bacillus brevis*.

In additional embodiments, the gaseous emission comprises, in addition to methane, a non-methane compound, wherein the non-methane compound is an organic or inorganic compound or material or substance. In another embodiment, the gaseous emission comprises a non-methane compound or substance such as toluene, benzene, methanol, propylene, alkenes, alcohol, ether, ethane, propane, butane, isobutane, formaldehyde, and trichloroethylene, or a combination thereof. Non-methane compounds or substances may also include non-methane gases such as carbon dioxide, oxygen, nitrogen, ammonia, nitrous oxide, and ozone.

In several embodiments, the non-methane compound or substance is metabolized, consumed, or used by the methanotrophic microorganisms. In several embodiments, the non-methane compound or substance is produced intracellularly. In several embodiments, the non-methane compound or substance is present in the growth medium at a concentration of less than 100,000 part per million (ppm), less than 10,000 ppm, less than 1000 ppm, less than 100 ppm, less than 10 ppm, less than 1 ppm, less than 100 part per billion (ppb), less than 10 ppb, or less than 1 ppb.

In several embodiments, the invention comprises reducing the concentration of methane to a concentration compliant with applicable environmental regulations or laws. In the United States, for example, preferred embodiments of the invention reduce methane to concentrations suggested or mandated by local, state, and federal EPA guidelines.

In several embodiments, the present invention comprises a method of producing a commercially useful biodegradable polymer from landfill gas. In some embodiments, the method comprises obtaining landfill gas, wherein the landfill gas comprises methane, enclosing the landfill gas in a bioreactor containing methanotrophic microorganisms and growth medium, and inducing the methanotrophic microorganisms to produce biodegradable polymer by controlling, substantially reducing, or depleting the growth medium of one or more compounds, elements, or nutrients necessary for growth of the methanotrophic microorganisms. As disclosed herein, all of the various components (including elements, compounds, liquids, gases, solids, and other compositions) of a culture medium can be considered an essential nutrient, given that they support the growth of the microorganisms (such as carbon, oxygen, magnesium, phosphorus, phosphate, potassium, sulfate, sulfur, calcium, boron, aluminum, chromium, cobalt, iron, copper, nickel, manganese, molybdenum, sodium, nitrogen, nitrate, ammonia, ammonium, urea, amino acids, methane, carbon dioxide, and/or hydrogen). In one embodiment, the method further comprises harvesting the biodegradable polymer (or other product).

In several embodiments of the present invention, a system to reduce methane emissions or gaseous emissions comprising methane is provided. In some embodiments, the emissions are produced by landfills, waste processing sites, coal mines, and/or other similar systems created by humans.

Thus, in accordance with several embodiments, methane-containing gaseous emissions are used as a source of carbon and/or energy for the induction of a methane-driven process and/or for the production of methane-derived materials, such as methane-utilizing microorganisms, heat, and/or electricity.

As discussed previously, methane is an environmentally-destructive material and previously unusable source of energy, which, according to several preferred embodiments of the invention, is used to produce a useful end-product that can be used or sold for use, providing an economic incentive for methane emissions reduction efforts on various scales and from various sources. In one embodiment, the end-product is heat. In another embodiment, the end-product is fuel. In yet another embodiment, the end-product is electricity. In yet another embodiment, the end-product is another form of energy. In further embodiments, the end-product is the culture of microorganisms or a byproduct isolated from the culture.

The term "air" as used herein shall be given its ordinary meaning, and shall include all airborne and gaseous components of air that have been contacted with or comprise methane, as well as ammonia gas, dust, microorganisms, and/or other airborne materials that may be present in the air.

In several embodiments, the term methane-consumption means shall be given its ordinary meaning and shall also include any means by which the methane is oxidized, consumed, and/or otherwise used as a form of carbon and/or energy. For example, methane-consumption means includes, but is not limited to, methane-utilizing microorganisms, fuel cells, turbines, reverse-flow reactors, engines, microturbines, and/or any other mode of using and/or consuming methane. Accordingly, in some embodiments, methane emissions are conveyed from a source to one or more of fuel cells, turbines, reverse-flow reactors, engines, or microturbines to produce fuel or other energy. Thus, in some embodiments, methanotrophic microorganisms need not be used.

In one embodiment, the ammonia contained within the air is contacted with liquid water and converted into ammonium and used as a source of nitrogen by the methane-utilizing microorganisms. In one embodiment, the dust and/or other airborne material within the air is reduced prior to or in the course of using the methane within the air as a source of carbon and/or energy.

In one embodiment, methane from a first source is used by the methane-consumption means in conjunction with one or more supplemental sources of methane, such as coal mine methane, landfill gas methane, natural gas methane, manure digester methane, wastewater treatment methane, and/or other sources of methane.

In one embodiment, a conveyor is provided to direct, move, and/or otherwise convey methane containing air or a methane containing gaseous emission, wherein the conveyor can be used to contact the methane with the methane consumption means. In another embodiment, a conveyer is used to move gaseous and/or methane emissions from one location to another, and may include one or more of pipes, tubing, one or more containment areas or compartments, ducts, channels, ventilation air or gas moving devices (e.g., fans, vacuums, etc.), and other conduits. In one embodiment, the conveyer is large and/or compartmentalized such that at least a portion of the conveyer serves as a bioreactor, in that it contains methanotrophic organisms.

In one embodiment, the methane emissions provided to the methanotrophic organisms or other methane consumption means is provided in conjunction with air, dust, methane, ammonia, gases, insects, particulate matter, and/or other airborne matter. In some embodiments, one of skill in the art will appreciate that one or more of the above steps described herein is modified or omitted. Further, the steps need not be conducted in the order set forth herein.

DETAILED DESCRIPTION

While this invention comprises embodiments in many different forms, there will herein be described in detail preferred methods of carrying out a process (or an associated system) in accordance with several embodiments of the invention with the understanding that the present disclosure is to be considered as an exemplification of the principles of the invention and is not intended to limit the broad aspect of the invention to the embodiments illustrated.

In a preferred embodiment of the invention, methane emissions are treated through the use of a product-generating methanotrophic growth system. In one embodiment, this growth system is designed to enable the production of harvestable bio-based goods. For example, in a preferred embodiment, methanotrophic microorganisms and air containing methane emissions are mutually-exposed to one another in an apparatus, such as a bioreactor, filled with methanotrophic bacteria, whereby methanotrophic bacteria use methane emissions for the creation of a harvestable bio-based product. In several embodiments, the processes and systems disclosed herein are advantageous in that the harvestable products generated are consistent over time (e.g., the functional properties of a product (or products) is predictable and substantially uniform from batch to batch).

In one embodiment, the harvestable bio-based product includes, but is not limited to, a polymer such as polyhydroxybutyrate (PHB), single cell protein, enzymes, homogenized biomass, methanotrophic cultures, and other harvestable methanotrophic products (e.g., a harvested enzyme, such as methane monooxygenase), or combinations thereof. For example, the methods disclosed herein allow a final product that has consistent characteristics despite the dynamic nature of a microorganism culture over time (e.g., the culture may undergo changes in population density, dominance of the culture by one or more species of microorganism within the culture, etc.). The dynamic nature of a microorganism culture, in the absence of the methods disclosed herein, leads to a dynamic (e.g., inconsistent) product. Such product inconsistency is associated with poor overall quality control and potentially reduced product value, as well as commercial non-viability. In several embodiments, the methods disclosed herein reduce the variability of one or more of the products produced by a microorganism culture.

In several embodiments, the functional properties of the products are consistent over time. As used herein, the terms "functional properties" and "functional characteristics" shall be given their ordinary meanings and shall also refer to the specification, features, qualities, traits, or attributes of the product. For example, in several embodiments, polymers are generated as a product. The functional characteristics of the generated polymers include, but are not limited to molecular weight, polydispersity and/or polydispersity index, melt flow and/or melt index, monomer composition, co-polymer structure, melt index, non-PHA material concentration, purity, impact strength, density, specific viscosity, viscosity resistance, acid resistance, mechanical shear strength, flexular modulus, elongation at break, freeze-thaw stability, processing conditions tolerance, shelf-life/stability, hygroscopicity, and color. As used herein, the term "polydispersity index" (or PDI), shall be given its ordinary meaning and shall be considered a measure of the distribution of molecular mass of a given polymer sample (calculated as the weight average molecular weight divided by the number average molecular weight). Advantageously, several embodiments of the processes disclosed herein may be carried out in sterile, semi-sterile, or non-sterile conditions.

In several embodiments, the processes and systems disclosed herein are optimized to produce harvestable products that have similar functional properties. In some embodiments, "similar" or "substantially similar" properties are those that differ by less than about 75% to about 65%, less than about 65% to about 55%, less than about 55% to about 45%, less than about 45% to about 35%, less than about 35% to about 25%, less than about 25% to about 20%, less than about 20% to about 15%, less than about 15% to about 10%, less than about 10% to about 5%, less than about 5% to about 1%, less than about 1% to about 0.1% from batch to batch, culture to culture, sample to sample, or moment to moment. In several embodiments, the functional properties of the products is substantially similar over time, e.g., essentially indistinguishable from batch to batch, culture to culture, or moment to moment.

The term "harvestable" as used herein shall be given its ordinary meaning and shall also mean usable, producible, collectable, useful, yieldable, consistent, defined, commercially useful, functional, and capable of being harvested. Likewise the term "harvest" is a broad term that shall be given its ordinary meaning and shall also mean gather, collect, amass, accumulate, assemble, purify, isolate, use, etc.

In one embodiment, methane emissions are captured, exposed to, and treated with one or more species of methanotrophic microorganisms to produce a harvestable single cell protein. Single cell protein (SCP) includes microbial biomass or proteins containing therein or extracted therefrom, and may be used as animal feed, for human nutrition, or for industrial uses. One particularly suitable method for the production of single cell protein is the use of a self-containing conglomerate of microorganisms that promotes product and species stability in non-sterile or semi-sterile conditions. The production process used by Norferm A/S in Norway to create SCP from methane is one example of a methanotrophic growth process that may be applied to carry out one embodiment of the present invention.

Another suitable method for the production of a harvestable product (including, but not limited to SCP) is the use of methods disclosed herein to promote product stability (e.g., consistency over time in the face of changing conditions in the microorganism culture) and harvestability. These methods include, but are not limited to: air disinfection, water disinfection, mineral media disinfection, system sterility management, directed species symbiosis, growth conditions management (e.g., manipulation or changing the formulation of the growth culture media, or other factors that influence the culturing environment), incoming air gaseous components separation, and others. Accordingly, in one embodiment, product stability and/or harvestability is enhanced or facilitated by one or more of these methods. For example, in several embodiments, the culture media which is initially used to culture methanotrophic microorganism may later be altered (e.g., concentrations of one or more constituents increased, decreased, removed or newly introduced) in order to induce the culture to respond in a certain, uniform (e.g., across the majority of the culture) fashion, and thereby produce a desired product.

For example, in several embodiments, methane emissions are used to effect the growth of microorganisms, wherein microorganisms are subsequently manipulated to produce harvestable PHB by controlling the concentration of a particular nutrient, nutrients, or combinations thereof, such as nitrogen, magnesium, phosphorus, oxygen, carbon, potassium, sulfate and/or iron, in the culture on a batch, semi-batch, or continuous basis. As discussed above, as the microorganisms are dependent on the nutrients (including elements and other compositions) provided in a growth culture media, each component of the media can be considered an essential nutrient. As such, the manipulation or control of (which includes increasing the concentration of, decreasing the concentration of, depleting the media of such, or newly introducing such) one or more essential nutrient is used in several embodiments to cause a culture to metabolically respond in a known and consistent manner, thereby ensuring predictable and consistent product generation. In several embodiments, temporal aspects of a how a microorganism culture is treated are important. For example, a particular nutrient may be present in a growth culture medium at the outset of culturing, when maintenance of the culture is the primary goal. At a later time, alteration of the concentration of that particular nutrient (alone or in combination with alterations of other nutrients) is used to covert the culture from a simple growth culture to a culture producing a desired product. Methanotrophic microorganisms (such as *Methylocystis parvus* or *Alcaligenes eutrophus*) generate or employ a polymer (such as PHB) as a form of an energy storage molecule to be metabolized when other common energy sources are not available. As is well known in the art of microbial PHA and PHB production, the depletion of an essential nutrient such as nitrogen (or other nutrient, essential nutrient, element, or compound present in a growth culture media) in the presence of a sufficient carbon supply will cause bacterial cultures to store energy in the form of PHA, PHB, or, depending on growth conditions, some similar energy storage material, with the aim of accessing this stored energy once all essential growth and reproduction components are fully present at a later time. Thus, in one embodiment, methanotrophic organisms are periodically or continuously exposed to methane emissions in a nutrient (e.g., nitrogen)-poor environment to effect PHA production. Partial, substantial, or complete depletion of nitrogen (or other nutrient, such as magnesium, phosphorus, potassium, zinc, sulfate, oxygen) occurs before the organisms are exposed to methane in some embodiments, or in other embodiments, after such exposure has occurred, in order to effect PHA production. Alternatively, nutrient (e.g., nitrogen, magnesium, phosphorus, potassium, zinc, sulfate, oxygen, or other nutrient) depletion can occur at some point during exposure of the organisms to methane in order to effect PHA production. PHB, or similar energy storage materials, such as polyhydroxybutyrate (PHB), polyhydroxybutyrate-covalerate (PHBV), poly-4-hydroxybutyrate (P4HB), polyhydroxyhexanoate (PHHx), and polyhydroxyoctanoate (PHO), or other PHAs, may account for a significant percentage of the weight and/or volume of a single microorganism cell, and may be harvested by any number of well known techniques, such as centrifugation, cell lysis, homogenization, chloroform dissolution, sodium hydroxide dissolution, cell parts extraction, and so on.

In another embodiment of the invention, methanotrophic microorganisms are used to oxidize a quantifiable, monitored, and certifiable volume of methane in a sterile or non-sterile environment, including at a specified rate, thereby creating a greenhouse gas reduction product which may be "harvested" and sold in a market which purchases and/or trades greenhouse gas reduction credits, such as a carbon dioxide or carbon dioxide equivalent credit trading market. Thus, in one embodiment, the harvestable product is the quantifiable reduction of methane, especially as it pertains to air pollution reductions credits and/or global warming gas emissions reductions credits. Accordingly, in one embodiment of the invention, a system to quantify how much methane has been used is provided. Such embodiments are particularly advantageous for those organizations that need to comply with certain environmental regulations or need to certify that specific volumes of methane have been biologically oxidized.

In an additional embodiment of the invention, methane emissions may be used to create harvestable enzymes, either alone or in conjunction with the other harvestable products disclosed herein. In several embodiments, the enzyme is methane monooxygenase. In some embodiments, the methane monooxygenase is in a particulate form, while in some embodiments, it is in a soluble form. In one embodiment, the cellular contents of methanotrophic microorganisms is accessed physically, chemically, enzymatically, or otherwise to enable harvesting cell contents from defined (or, optionally, non-defined) microbial cultures. By way of example, controlling the concentration of copper (e.g., increasing, decreasing, or maintaining) in the growth culture media within certain ranges of concentrations is useful, in several embodiments, to effect the consistent production of either soluble or particulate methane monooxygenase, as is well known in the art. In particular, in some embodiments, if the concentration of copper in a methanotrophic growth medium is minimized and kept below specific concentrations, such as $5 \times 10^{-9}$ M, the production of soluble methane monooxygenase may be effected in most, substantially all, or all methanotrophic cells accessing that copper-limited medium. In some embodiments, copper and optionally at least one or more additional nutrient are maintained at specific concentrations in order to effect a consistent ratio of sMMO and pMMO in a culture of methanotrophic microorganisms. In some embodiments, the production of pMMO may be effected in most or all of the methanotrophic cells and the production of sMMO may be substantially eliminated in most or all of the methanotrophic cells. In other words, a varied and dynamic culture of methanotrophic microorganisms (e.g., in different stages of growth or employing different active metabolic pathways) can, in some embodiments, be rendered more metabolically consistent (e.g., the majority of the culture is induced to metabolize methane through, for example, particulate methane monooxygenase) by manipulating the concentrations of copper (and, optionally, other nutrients, including nutrients or compounds/substances that chelate copper and thereby render them non-available to microorganisms) in the media. In some embodiments, the methane monooxygenase is the desired harvestable product. Soluble or particulate methane monooxygenase may be harvested using any well known methane monooxygenase extraction and purification method.

In some embodiments, sMMO is expressed in a range between about 0% and 100% of a methanotrophic culture by dry cell weight, as a percentage of microorganisms expressing sMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof. Simultaneously, or independently, in some embodiments, pMMO is expressed in a range between about 0% and 100% of a methanotrophic culture by dry cell weight, as a percentage of microorganisms expressing pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof. In some embodiments, the ratio of sMMO to pMMO produced in a methanotrophic culture is controlled to control the specification of PHA produced by a culture. In some embodiments, the relative weight ratio of sMMO to pMMO in a methanotrophic culture is at least or approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1, respectively. In some embodiments, the relative weight ratio of pMMO to sMMO in a methanotrophic culture is approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1.

In some embodiments, by controlling the relative concentrations of sMMO and pMMO produced by a culture of methanotrophic microorganisms, it is possible to control the metabolic status of the culture and thereby control the type of PHA and other cellular material produced by the culture, particularly in the presence of one or more of the following: volatile organic compounds, fatty acids, volatile fatty acids, PHAs, hydroxyalkanoates, butyrate, hydroxybutyrate, polyhydroxybutyrate, valerate, hyroxyvalerate, valeric acid, butyric acid, polyhydroxybutyrate-covalerate, hexanol, heptanol, lauric acid, methanol, formate, formaldehyde, propane, ethane, butane, isobutane, acetone, acetate, acetic acid, formic acid, dissolved carbon dioxide, dissolved methane, dissolved oxygen, carbon-containing materials, ammonia, ammonium, and other elements or compounds or substances that impact the metabolism of a culture of methanotrophic microorganisms in a certain manner, including according to the relative concentration of sMMO or pMMO in such a culture. In some embodiments, sMMO and/or pMMO is expressed in a range between about 0% and 100% of a methanotrophic culture by dry cell weight, as a percentage of microorganisms expressing sMMO or pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof prior to, during, throughout, or after a PHA production phase.

In one embodiment, sMMO is not expressed, or is expressed in low concentrations (e.g., less than 5%, 3% or 1%), in a methanotrophic culture prior to, during, throughout, or after a PHA production phase. In some embodiments, the directed or controlled absence or reduction of sMMO in a methanotrophic culture producing PHA, particularly in the presence of non-methane organic compounds or substances that can be metabolized by methanotrophic microorganisms, engenders PHA production stability, consistency, and control by selectively shielding against the metabolism of one or some or many non-methane organic compounds or substances that might otherwise be metabolized in the presence of sMMO, which enables the metabolism of a larger group of non-methane compounds or substances than pMMO. Further, in some methanotrophic cultures and some embodiments of the invention, pMMO promotes PHA synthesis at high intracellular concentrations by reducing cellular production of non-PHA materials, particularly as compared to PHA synthesis using sMMO. Similarly, in one embodiment, pMMO is not expressed, or is expressed in low concentrations (e.g., less than 5%, 3% or 1%), in a methanotrophic culture prior to, during, throughout, or after a PHA production phase. In some embodiments, the directed or controlled absence or reduction of pMMO in a methanotrophic culture producing PHA, particularly in the presence of non-methane compounds or substances (organic or inorganic) that can be metabolized by methanotrophic microorganisms, engenders PHA production stability, consistency, and control by selectively inducing or promoting the metabolism of one or some or many non-methane organic compounds that might otherwise be not be metabolized using pMMO. Further, in some methanotrophic cultures, sMMO promotes PHA synthesis at high intracellular concentrations by reducing cellular production of non-PHA materials, particularly as compared to PHA synthesis using pMMO. By controlling the concentration of sMMO relative to pMMO in a methanotrophic microorganism culture in the presence of methane and/or non-methane organic or inorganic compounds, including VOCs, volatile fatty acids, methanol, formaldehyde, acetone, formate, ethane, propane, alkanoic acids, or carbon dioxide, it is possible to control the specification or type of PHA produced by the culture, including the molecular weight, polydispersity, and other similar functional characteristics. In some embodiments, it is preferable to maintain the concentration of copper in the culture media in order to promote sMMO production. In some embodiments, the production of sMMO in many, most, or substantially all of the methanotrophic cells enables the culture to produce more PHA when subject to a nutrient limiting step than would otherwise be produced if the relative ratio of pMMO in the culture was higher prior to the nutrient limiting step. In some embodiments, it is preferable to maintain the concentration of copper in the culture media in order to promote pMMO production. In some embodiments, the production of pMMO in many, most, or substantially all of the methanotrophic cells enables the culture to produce more PHA when subject to a nutrient limiting step than would otherwise be produced if the relative ratio of sMMO in the culture was higher prior to the nutrient limiting step. In one embodiment, one or more methanotrophic cells or cultures are subject to repeated growth and PHA synthesis cycles or steps, wherein the production of methane monooxygenase is followed by the production of PHA, wherein such cycling order is repeated over at least two consecutive cycles, and wherein the relative concentration of sMMO to pMMO in the cells or cultures is controlled or caused to remain approximately similar (e.g., within about 5% to about 10%, with about 10% to about 20%, within about 20% to about 30%, within about 30% to about 40%, within about 40% to about 50%, within about 50 to about 75%) or the same in each new cycle or step in order to control the functional properties of the PHA produced by or extractable from the culture or cultures in each new or repetitive cycle with the same or new cells.

In certain embodiments, as discussed above, the control of the concentration of one or more essential nutrients results in the production of a desired type of methane monooxygenase. In some embodiments, the production of the desired type of methane monooxygenase is followed by the controlling (e.g., increase, decrease, or maintenance) of an essential nutrient that results in the induction of PHA production. In some embodiments, these two steps performed consecutively can be considered a production cycle. In some embodiments, the first essential nutrient is the same as the second essential nutrient. In some embodiments, the concentration is controlled in the same fashion between the steps of the production cycle, but to different degrees (e.g., reduced by 20% in the first step and by a further 20% in the second step). In other embodiments, the concentration is controlled in different fashion (e.g., increased in one step and decreased in the other) to the same or varying degrees. As used herein, the term "production cycle" shall be given its ordinary meaning, and shall also refer to the sequential steps that result in the production of PHA having consistent functional properties. In some embodiments of the methods disclosed herein a single production cycle is used, while another by embodiments, a plurality of production cycles is performed. In some embodiments, additional steps are included in the production cycle. In some embodiments the repetition of production cycles improves the overall PHA (or other product) quality (e.g., purity, functional performance) and/or output (e.g., rate or yield of production) for a given amount of input material (methane emissions or other methane-containing gas), including by selecting for, controlling, and/or enhancing the metabolic disposition of the microorganism culture to produce PHA at higher quaity, rates, or yield for a given input material.

In several embodiments of the invention, a culture is induced to maximize the production and intracellular concentration of PHA in the culture by controlling the concentrations of essential nutrients and/or chemicals in the medium and causing the culture to expel non-PHA biomass material, including water-soluble material, into the medium, thereby increasing the concentration of PHA in the culture to greater than 70% PHA, greater, than 80% PHA, greater than 85% PHA, greater than 90% PHA, greater than 95% PHA, or greater than 99% PHA. In another embodiment of the invention, the culture is induced to maximize the production and intracellular concentration of PHA in the culture by controlling the concentrations of essential nutrients and/or chemicals in the medium and causing the culture to synthesize PHA to very high concentrations, increasing the concentration of PHA in said culture to greater than 70% PHA, greater, than 80% PHA, greater than 85% PHA, greater than 90% PHA, greater than 95% PHA, or greater than 99% PHA. In one embodiment, PHA-biomass may or may not be subjected to one or more extraction techniques in various degrees, steps, or combinations, such as solvent extraction, super critical carbon dioxide extraction, non-polymer cellular material dissolution extraction, or other extraction techniques. In one embodiment, non-PHA biomass material expelled into the mineral medium is separated from the PHA-rich culture material by one or more separation mechanisms, including, but not limited to liquid-liquid and liquid-solid separation (e.g., filtration, centrifugation, reverse osmosis, ultrafiltration, distillation, etc.). In one embodiment of the invention, the culture is induced to solubilize non-PHA material into the medium by controlling the concentrations of one or more essential nutrients and/or chemicals in the medium. In one embodiment, solubilized non-PHA biomass material is separated from PHA by various separation mechanisms, including liquid-liquid and liquid-solid separation (e.g., filtration, centrifugation, distillation, etc.). In one embodiment, the culture is induced to increase the concentration of PHA as a percentage of solid material in the medium by controlling the concentrations of one or more essential nutrients or chemicals in the medium, thereby causing the culture to a) expel non-PHA material into the mineral medium, b) solubilize non-PHA material into water-soluble material, c) expel water-soluble non-PHA material into the medium, and/or d) dissolve non-PHA material into the medium.

Likewise, in some embodiments, adjusting the growth culture medium with respect to other compounds, substances, or nutrients can impact the cultured microorganism in other beneficial ways (e.g., to induce production of another or an alternative product). As discussed above, in several embodiments, the concentration of one or more essential nutrients is adjusted (e.g., increased, decreased, or depleted) in the media, which, in several embodiments, causes the microorganisms to store energy in the form of a polymer, which can thereafter be harvested. In some embodiments, the manipulation of the culture environment in which all the microorganisms of a given culture are growing or maintaining an active or responsive metabolic state allows a large portion (if not all) of the microorganisms in the culture to respond to the manipulation in a uniform fashion (e.g., most or all store energy as PHA), which leads to more uniform products, due, at least in part, to the uniformity of the microorganism response. In some embodiments, between about 30% and about 50%, between about 50% and about 70%, between about 70% and about 80%, between about 80% and about 90%, between about 90% and about 95%, between about 95% and about or 100% (and overlapping ranges thereof) of the culture responds to a change (or maintenance) of certain culture conditions in the same (or a substantially similar) fashion.

The processes disclosed herein may be carried out and directed in a controlled bioreactor, wherein liquid, semi-liquid, particulate, or solid mineral media may be used to enhance the growth of methanotrophic microorganisms. Alternatively, the processes described herein may be carried out in reaction tanks, vessels, fixed film reactors, trickle bed reactors, foam reactors, or any other appropriate culture/containment systems.

In additional embodiments, various processing techniques known in the art may or may not be used to preferentially extract (e.g., remove biomass or biocatalyst from) harvestable products of methanotrophic growth, such as chemical treatment, centrifugation, drying, and homogenization. In some embodiments, extraction agents or mechanisms are selected from the group consisting of: methylene chloride, acetone, ethanol, methanol, dichloroethane, supercritical carbon dioxide, sonication, homogenization, water, heat, distillation, spray drying, freeze drying, centrifugation, filtration, enzymes, surfactants, hydrolyzers, acids, bases, hypochlorite, peroxides, bleaches, ozone, EDTA, and/or combinations thereof.

In one embodiment, the extraction process may be substantially carried out at intracellular temperatures less than 100° C. In other embodiments, temperatures for extraction range from about 10° C. to about 30° C., from about 30° C. to about 50° C., from about 50° C. to about 70° C., from about 70° C. to about 90° C., from about 90° C. to about 120° C., from about 100° C. to about 140° C., from about 20° C. to about 150° C., or from about 120° C. to about 200° C., or higher. In another embodiment, cells and/or biocatalyst are reused for polymerization following the extraction process as viable cells or catalytic material.

In a several preferred embodiments of the invention, landfill gas is used as the source of methane. In one embodiment, impurities from landfill gas, such as non-methane and/or volatile organic compounds, water vapor, and/or carbon dioxide are partially, substantially, or completely removed. In another embodiment, the landfill gas is disinfected. In one embodiment, UV treatment is used to disinfect the gas. Mechanical, activated carbon, or chemical filtration may also be used. However, in several embodiments the landfill gas is used without purification, disinfection, or other such manipulation.

In several embodiments, methane emissions within landfill gas (or other source of methane) are exposed to methanotrophic microorganisms. In one embodiment, gaseous emissions comprising methane are fed into a bioreactor containing methanotrophic microorganisms suspended in or on a liquid, semi-liquid, or solid growth-culture medium containing growth media comprising essential nutrients. In another embodiment, after methanotrophic microorganisms have grown and reproduced using methane emissions as a source of carbon and/or energy, these microorganisms are harvested as single cell protein through various extraction and de-watering processes. In some embodiments, non-methane components within methane emissions, such as methanol, acetone, acetate, formate, formaldehyde, hydroxyalkanoates, hydroxybutyrate, octanoic acid, octanol, carbon dioxide, nitrogen, oxygen, di-oxygen, di-nitrogen, water, water vapor, argon, ethane, propane, butyrate, butyric acid, hexanoic acid, hexanol, heptanoic acid, heptanol, pentane, pentanoic acid, and volatile organic compounds, are used to modify the functional and/or molecular characteristics of PHA produced by a microorganism culture, e.g., causing methanotrophic microorganisms to produce various types of PHAs, such as polyhydroxybutyrate (PHB), high ultra high molecular weight PHB, polyhydroxybutyrate-covalerate (PHBV), poly-4-hydroxybutyrate (P4HB), poly-hydroxyhexanoate (PHHx), and polyhydroxyoctanoate (PHO), or other PHAs with enhanced or modified properties according to the kinds of non-methane components exposed to the methanotrophic microorganisms.

In several embodiments, a method of treating gaseous emissions (e.g., landfill gas) is provided. In one embodiment, the method comprises: (i) enclosing the landfill gas in a bioreactor containing methanotrophic microorganisms; and (ii) harvesting the microorganisms and/or the products produced by the microorganisms in the bioreactor. In another embodiment, the method comprises: (i) removing impurities from the landfill gas; (ii) disinfecting the landfill gas; (iii) enclosing the landfill gas in a bioreactor containing methanotrophic microorganisms; and (iv) harvesting the microorganisms and/or the products produced by the microorganisms in the bioreactor.

In several embodiments, a portion of the microorganisms comprising sMMO and/or pMMO are directed into a bioreactor, or another phase of bioreactor operation, containing or comprising a nitrogen depleted growth medium (or a medium deprived of one or more other essential nutrients) and a constant supply of gaseous emissions (e.g., landfill gas), whereby the microorganisms synthesize intracellular PHA (e.g., PHB). In one embodiment, the PHB-filled cells are subsequently removed from the reactor in order to process and harvest the material into commercially useful form. These processes are preferentially carried out on a continuous, semi-continuous, semi-batch, or batch-wise basis, using methane emissions from any source, including, but not limited to landfills, coal mines, wastewater treatment plants, agricultural systems, petroleum systems, or other sources.

As used herein, the term "methanotrophic microorganisms" shall be given its ordinary meaning and shall also refer to any microorganisms that utilize methane as a source of carbon and/or energy for growth and reproduction, including naturally-occurring and/or genetically engineered microorganisms. It shall also refer to the combination or mixture of methanotrophic and non-methanotrophic microorganisms that promote the growth of methanotrophic microorganisms. In one preferred embodiment, this combination comprises *Methylococcus capsulatus, Alcaligenes acidovorans, Bacillus firmus*, and *Bacillus brevis*, since this combination has been shown to limit or reduce bacterial contamination in non- and semi-sterile bioreactor conditions, thereby enabling stable product formation. In another preferred embodiment, this combination comprises any methanotrophic microorganisms, such as Type II methanotrophic microorganisms, including from the genus *Methylocystis* and *Methylosinus* that may be preferentially used to produce polymers such as PHB, enzymes such as methane monooxygenase, and/or any other cellular components. In another preferred embodiment, this combination comprises a non-defined mix of methanotrophic and non-methanotrophic microorganisms that can be used to create a harvestable product from the oxidation (or alternate processing) of methane emissions.

The terms "methanotrophic microorganism growth-culture medium" and "growth medium" shall be given their ordinary meaning and shall also refer to any medium promoting the growth of microorganisms. The terms shall also refer to any substrate, aside from methane, which microorganisms oxidize or otherwise break down. It shall also refer to any substrate or material that concentrates methane, preferentially sequesters methane, "traps" methane, increases the solubility and/or availability of methane, and/or otherwise enables the enhanced breakdown, oxidation, and/or utilization of methane by microorganisms. The term "microorganism growth-culture medium" includes, but is not limited to, any substrate and/or microorganism immobilization means, such as liquid, semi-liquid, gas, particulate, ceramic, foam, plastic, alginate gel, fixed film, attached biofilm, methanol-enriched, copper-enriched, clay, nutrient, or other appropriate growth-culture medium. In one preferred embodiment, this growth culture medium comprises an aqueous solution containing water, nitrogen, ammonium, trace minerals, and other well-known microorganism growth-culture medium components necessary for the growth and reproduction of methane-utilizing bacteria (e.g., essential nutrients), such as, for example, carbon, oxygen, magnesium, phosphorus, phosphate, potassium, sulfate, sulfur, calcium, boron, aluminum, chromium, cobalt, iron, copper, nickel, manganese, molybdenum, sodium, nitrate, ammonia, ammonium, urea, amino acids, methane, carbon dioxide, and/or hydrogen. In another preferred embodiment, this growth culture medium comprises a microorganism immobilization means, such as organic or inorganic particles, on which a liquid or semi-liquid mineral medium solution is continuously or periodically contacted and on which microorganisms are attached. In another preferred embodiment, this growth-culture medium comprises waste organic materials, which methane-utilizing microorganisms may or may not break down to produce a byproduct of organic materials that may or may not be useful. In another preferred embodiment, this growth-culture medium comprises a liquid foam substrate.

As is well-known in the art, the various components of a growth-culture medium consist of those compounds, substances, salts, elements, and other nutrients that are essential for the continued viability and growth of methanotrophic microorganisms.

In another preferred embodiment, a system comprising methanotrophic organisms is used to degrade or otherwise reduce a pollutant other than methane as a method to enable the viable treatment of methane emissions. In one embodiment, the growth of methanotrophic microorganisms using methane emissions is carried out in the presence of a non-methane material that can be broken-down, oxidized, consumed, and/or otherwise changed in form through the action of such microorganisms. In several embodiments, the non-methane material includes, but is not limited to, one or more of the following: toluene, benzene, methanol, propylene, any alkenes, alcohols, ethers, alicyclics, aromatics, and/or chlorinated organic compounds, such as the pollutant TCE. As discussed herein, the resultant product(s), including the oxidized chemical or quantifiable pollutant treatment, may be harvested in a controlled, directed, and/or quantifiable manner.

In another preferred embodiment of the invention, following the growth of methanotrophic microorganisms in a bioreactor (or other appropriate apparatus), some or all of the contents of the bioreactor are removed from the bioreactor and are either processed or used and sold directly. Processing may include any number of methods that enable product harvest, such as centrifugation, filtration, drying, homogenization, chemical treatment, physical treatment, enzymatic treatment, or any other processing means. Processing means may be used to extract products out of defined or non-defined conglomerates of methanotrophic microorganisms. The application and utilization of such processing techniques, such as, for example, centrifugation and homogenization, may be used to effect the overall harvestability of the methanotrophic growth and treatment process, especially where the maintenance of a defined culture is unfeasible or otherwise impractical. For example, if a methanotrophic culture is particularly varied (e.g., a large number of species) or dynamic over time due to changing culture conditions, a portion of the culture can be removed at a first point in time, processed to obtain a desired product and stored. Thereafter, a subsequent portion of the culture can be removed at a time when the desired product is again being produced by the culture, and optionally combined with the first batch of product. In this manner a more consistent product over time can be obtained from a varied culture through application of the various processing means disclosed herein.

Preferred embodiments of the present invention offer one or more advantages. For example, one or more embodiments provide one or more of the following benefits:

(i) enables the viable and economical treatment of methane emissions;

(ii) enables the viable and economical application of methanotrophic microorganisms to methane emissions treatment in environments, particularly for methane emissions streams where the concentration of methane is low, variable, impure, or unpredictable;

(iii) provides a methanotrophic methane emissions treatment process that is economically competitive with alternative methods of methane emissions treatment;

(iv) overcomes previously insurmountable practical challenges in the field of methane emissions treatment, particularly for low-quality, low purity, or low-BTU methane emissions treatment; and/or (v) provides a process which, if widely applied, has the capacity to significantly reduce global methane emissions.

Preferred embodiments of the invention comprise one or more of the foregoing advantages and/or objects. Further objects and advantages will become apparent from the ensuing description.

In several embodiments, methane emissions may be used from a variety of sources or combinations of sources, including, but not limited to landfills, coal mines, wastewater treatment plants, manure digesters, agricultural digesters, compost heaps, enclosed agricultural feedlots, leaking or otherwise emitting petroleum systems, and any other source of methane emissions or off-gas whereby the creation of harvestable bio-based is enabled. The methane emitted by ruminant animals can also be used as a source of methane according to several embodiments. The processing of methane emissions produced by ruminant animals is discussed in greater details in U.S. Pat. No. 7,745,197, which is incorporated in its entirety by reference herein.

The term "consolidation means" shall be given its ordinary meaning and shall also refer to any means by which methane emissions are unified, mutually-directed, and/or otherwise consolidated for conveyance, movement, or storage. In one preferred embodiment, a consolidation means comprises an air-tight ducting tube running from an air outlet to a mutual-exposure means, as described below, wherein methane containing gas is directed from a first location, through a consolidation means, and into a mutual-exposure means. In another preferred embodiment, a consolidation means comprises multiple ducting tubes connected to air outlets and situated to consolidate methane containing gas into a single ducting tube that ultimately leads into a methane-consumption system.

The term "ventilation means" shall be given its ordinary meaning and shall also refer to any means by which air, gases, and/or other airborne material is mechanically forced, pushed, pulled, drawn, moved, conveyed, or otherwise directed into, through, and/or out of a first area (e.g., a source of methane containing gas) to a second area (e.g., a bioreactor).

The term "air inlet" shall be given its ordinary meaning and shall also refer to any location where air, gas, and/or other airborne material enters into an area or chamber that is fully or partially enclosed (e.g., a bioreactor).

The term "air outlet" shall be given its ordinary meaning and shall also refer to any location where air, gas, and/or other airborne material exits out an area or chamber that is fully or partially enclosed (e.g., a bioreactor).

Methane-utilizing microorganisms represent one embodiment of a "methane-consumption system" or "methane consumption means." The latter two terms shall be given their ordinary meaning and shall also refer to one or more biological systems that utilize enteric fermentation methane as a source of carbon and/or energy, a mechanical system that uses or consumes methane, and/or a chemical system that uses, degrades, consumes, or reacts with methane.

The term "methane-utilizing microorganism" or "methanotrophic microorganism" shall be used interchangeably, shall be given their ordinary meaning, and shall also refer to any microorganism, naturally-occurring or genetically-engineered, that utilizes methane, including enteric fermentation methane, as a source of carbon and/or energy. The term "methane-utilizing microorganisms" also refers to the combination of methane-utilizing and non-methane-utilizing microorganisms that are collectively associated with the growth of methane-utilizing microorganisms. In one embodiment, this microorganism combination includes one or more of the following: *Methylococcus capsulatus, Alcaligenes acidovorans, Bacillus firmus*, and *Bacillus brevis*. In one embodiment, a combination of these microorganisms is used because among other advantages, this combination is known to promote the long-term growth of *Methylococcus capsulatus*. The term "methane-utilizing microorganisms" also includes any methanotrophic organisms and organisms that use or "take-up" methane. In several embodiments, methane-utilizing microorganisms are confined in a microorganism holding tank containing methane-utilizing microorganisms and a microorganism growth-culture medium. in several embodiments, a biofiltration system containing methane-utilizing microorganisms is provided, wherein microorganisms either are or are not attached to a microorganism support substrate and are continuously or intermittently contacted with a microorganism growth-culture medium. In several embodiments, the microorganism are used in a bioreactor containing a microorganism growth-culture medium wherein the growth-culture medium is in liquid, foam, solid, semi-solid, or any other suitable form and methane-utilizing microorganisms are naturally-occurring and/or genetically engineered and may or may not have been selectively inserted as part of a pre-determined microbial consortium. While the use of a specified microorganism consortium may provide some benefits, and is used in some embodiments, in other embodiments, a non-specified and naturally-equilibrating consortium of one or more microorganisms is employed. Typical examples of methane-utilizing microorganisms useful in several embodiments of the present invention include, but are not limited to, bacteria and yeast.

Suitable yeasts include species from the genera *Candida, Hansenula, Torulopsis, Saccharomyces, Pichia,* 1-*Debaryomyces, Lipomyces, Cryptococcus, Nematospora,* and *Brettanomyces*. The preferred genera include *Candida, Hansenula, Torulopsis, Pichia,* and *Saccharomyces*. Examples of suitable species include: *Candida boidinii, Candida mycoderma, Candida utilis, Candida stellatoidea, Candida robusta, Candida claussenii, Candida rugosa, Brettanomyces petrophilium, Hansenula minuta, Hansenula saturnus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitratophila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis,* and/or *Saccharomyces fractum*.

Suitable bacteria include species from the genera *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus,* and *Methylocystis*. Preferred genera include *Bacillus, Pseudomonas, Protaminobacter, Micrococcus, Arthrobacter* and/or *Corynebacterium*. Examples of suitable species include: *Bacillus subtilus, Bacillus cereus, Bacillus aureus, Bacillus acidi, Bacillus urici, Bacillus coagulans, Bacillus mycoides, Bacillus circulans, Bacillus megaterium, Bacillus licheniformis, Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter parafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevib acterium lactofermentum, Brevibacterium paraffinolyticum, Brevibacterium ketoglutamicum,* and/or *Brevibacterium insectiphilium,* including, but not limited to, microorganisms that utilize the serine, ethylmalonyl-CoA, and/or ribulose monophosphate (RuMP) pathway(s).

The term "microorganism growth-culture medium" shall be given its ordinary meaning and shall also refer to any medium promoting the growth of microorganisms. It shall also refer to any substrate, aside from methane, which microorganisms oxidize or otherwise break down. It shall also refer to any substrate or material that concentrates methane, preferentially sequesters methane, "traps" methane, increases the solubility and/or availability of methane, and/or otherwise enables the enhanced breakdown, oxidation, and/or utilization of methane by microorganisms. The term "microorganism growth-culture medium" includes, but is not limited to, any substrate and/or microorganism immobilization means, such as liquid, semi-liquid, gas, particulate, ceramic, foam, plastic, alginate gel, methanol-enriched, copper-enriched, clay, nutrient, or other appropriate growth-culture medium. In one preferred embodiment, this growth culture medium comprises aqueous solution containing water, nitrogen, ammonium, trace minerals, and other well-known microorganism growth-culture medium components necessary for the growth and reproduction of methane-utilizing bacteria, such as, for example, carbon, oxygen, magnesium, phosphorus, phosphate, potassium, sulfate, sulfur, calcium, boron, aluminum, chromium, cobalt, iron, copper, nickel, manganese, molybdenum, sodium, nitrate, ammonia, ammonium, urea, amino acids, methane, carbon dioxide, and/or hydrogen. In another preferred embodiment, this growth culture medium comprises a microorganism immobilization means, such as organic or inorganic particles, on which a liquid or semi-liquid mineral medium solution is continuously or periodically contacted and on which microorganisms are attached. In another preferred embodiment, this growth-culture medium comprises waste organic materials, which methane-utilizing microorganisms may or may not break down to produce a byproduct of organic materials that may or may not be useful. In another preferred embodiment, this growth-culture medium comprises a liquid foam substrate.

In yet another preferred embodiment, the growth-culture medium is combined with various materials which methane-utilizing microorganisms may or may not convert to more desirable materials. Examples of various materials include, but are not limited to, toluene, trichloroethylene (TCE), propylene, and agricultural byproduct materials which microorganisms may preferentially breakdown or oxidize.

As discussed above, several embodiments of the methods and systems provided herein are advantageous in that low concentration, variable flow, unpredictable, or non-pure methane streams or emissions, previously unusable, are used for the conversion of methane into useful products (e.g., polymers, proteins, enzymes, heat, and/or electricity). In one embodiment, methane is capable of being used at a methane-in-air volumetric concentration down to abut 0.1% methane-in-air, specifically by methanotrophic microorganisms, catalytic reactors, and thermal flow-reversal reactors. Thus, systems such as those disclosed herein can be used, in some embodiments, as a way to utilize low-concentration sources of methane to produce polymers, proteins, enzymes, heat, electricity, and/or other defined and consistent products. Specifically, microturbines, fuel cells, reverse-flow reactors, methanotrophic microorganisms and other means capable of utilizing methane at low concentrations can be used as a methane-consumption means in accordance with several embodiments of the invention, allowing air containing low concentrations of methane to be used in an unadulterated state as viable feedstock fuel. Optionally, gas concentrators that increase methane-in-air concentrations of exhaust gas, including systems that supplement or add other sources of methane, are employed to increase methane concentrations to levels more suitable for use by a range of methane-consumption means. Thus, although one preferred embodiment details the use of methane-utilizing microorganism as a preferred methane-consumption means, in another embodiment, any number of methane-consumption means (or combinations thereof) may be employed in accordance with embodiments of the invention to convert air containing low concentrations of methane into useful products such as heat and/or electricity.

The following Example illustrates non-limiting embodiments of the present invention and is not intended in any way to limit the claimed invention. Moreover, the methods described in the following Example need not be performed in the sequence presented.

EXAMPLE 1

The following example describes the processing of methane emissions from a landfill site in accordance with several embodiments disclosed herein. It shall be appreciated by one of skill in the art that the method described herein can also be used for any site that produces methane, such as coal mines, wastewater treatment plants, manure digesters, agricultural digesters, compost heaps, enclosed agricultural feedlots, fossil fuel systems, or combinations thereof.

In one embodiment, a landfill site that produces methane emissions will be identified. Landfill gas extraction wells and/or blowers are employed to draw landfill gas out of the landfill using equipment and technology that is used by any landfill gas extraction or environmental services firm, such as LFG Technologies of Fairport, N.Y., USA or SCS Engineers of Long Beach, Calif., USA. In several embodiments, the methane content of the extracted landfill gas can be monitored for the production of methane using any methane detector commonly used by an environmental services firm. If the methane concentration is greater than about 0.1% to about 1.0%, the landfill will be deemed suitable for methane recovery and processing according to several embodiments disclosed herein. In some embodiments, the methane concentration is between about 10% and about 60%, including between about 10% and about 20%, between about 20% and 30%, between about 30% and 40%, or more preferably between about 40% and about 50%. In other embodiments, methane emissions comprise methane in a concentration in the range of about 0.1% to about 10% (including about 0.1% to about 1%, about 1% to about 2%, about 2% to about 3%, about 3% to about 4%, about 4% to about 5%, about 5% to about 6%, about 6% to about 7%, about 7% to about 8%, about 8% to about 9%, about 9% to about 10%, and overlapping ranges thereof) in the range of about 10% to about 20%, or in the range of about 20% to about 40%, or greater than about 20%. Landfill sites (or other sites) having methane concentrations less than about 0.1% and greater than about 60% may also be used in some embodiments of the invention.

After a suitable landfill site has been identified, the landfill gas will be captured from the landfill using an air compressor, blower, vacuum, or other suitable capturing means. Optionally, impurities will then be removed from the landfill gas. For example, non-methane organic or inorganic compounds or substances, such as methanol, acetone, acetate, formate, formaldehyde, hydroxyalkanoates, hydroxybutyrate, octanoic acid, octanol, carbon dioxide, nitrogen, oxygen, di-oxygen, di-nitrogen, water, water vapor, argon, ethane, propane, butyrate, butyric acid, hexanoic acid, hexanol, heptanoic acid, heptanol, pentane, pentanoic acid, and volatile organic compounds, can be removed by passing the landfill gas through activated carbon, leaving mostly methane and carbon dioxide as the main components of the landfill gas. Although impurities need not be removed in every embodiment of the invention, the removal of impurities is advantageous in some embodiments. One advantage of removing impurities (such as water vapor, volatile organic compounds, particulate materials, and/or carbon dioxide) is minimizing the possibility of hindering microorganism growth as microorganisms contact the landfill gas.

The landfill gas is optionally disinfected using UV light. In those embodiments in which impurities are removed, UV irradiation can be used before, after or during the removal process. UV irradiation may also be used in embodiments that do not employ impurities removal. UV light is believed to disinfect the landfill gas by disrupting the nucleic acid structures within microorganisms in the landfill gas, subsequently eliminating the capacity of these microorganisms to reproduce. Impurities removal and disinfection do not have to be employed, however, because methanotrophic microorganisms can and are genetically or metabolically equipped (or can be designed to be so equipped) to withstand a range of impurities.

The landfill gas (which in a preferred embodiment is purified and disinfected) as well as air or oxygen (which in one embodiment is purified and/or disinfected) will be fed into a self-contained enclosure using an air compressor, air blower, or similar means. The self-contained enclosure is preferably a bioreactor that contains at least one species of methanotrophic microorganisms and growth medium, wherein the growth medium contains one or more non-methane compound or substance such as methanol, acetone, acetate, formate, formaldehyde, hydroxyalkanoates, hydroxybutyrate, octanoic acid, octanol, carbon dioxide, nitrogen, oxygen, di-oxygen, di-nitrogen, water, water vapor, argon, ethane, propane, butyrate, butyric acid, hexanoic acid, hexanol, heptanoic acid, heptanol, pentane, pentanoic acid, or volatile organic compounds. The bioreactor is preferably sized to accommodate the flow rate of landfill gas to be treated. For example, a bioreactor treating 1000 cubic feet per minute of landfill gas should be approximately twice as large in volume as a bioreactor treating 500 cubic feet per minute of landfill gas. Preferably, a bioreactor treating 1000 cubic per minute of landfill gas will contain about 10,000-800,000 liters of growth medium containing suspended methanotrophic microorganisms. Growth medium can be a liquid, semi-liquid, or solid substrate. For example, the growth medium may be water containing growth nutrients such as nitrogen, magnesium, phosphorus, copper, iron, potassium, and trace minerals, in which microorganisms are suspended.

In one embodiment, the growth medium is tailored to meet the specification of the end-product of microorganism growth. If the bioreactor is being used or processed, according to an embodiment of the invention, to create soluble methane monooxygenase, for example, it will be preferable to keep the copper concentration in the growth medium sufficiently low, for example, below about $5 \times 10^{-9}$ M, which may be achieved through continuous monitoring of the growth medium, calculated metering of copper into the growth medium, metering of copper-containing water into the growth medium, or, e.g., calculated metering of copper chelating agent into the growth medium.

The growth medium solution may consist of water filled with a range of mineral salts (e.g., essential nutrients, such as carbon, hydrogen, nitrogen, oxygen, phosphorus, potassium, calcium, sodium, chlorine, methane, carbon dioxide, magnesium, iron, copper, sulfate, manganese, boron, zinc, aluminum, nickel, chromium, cobalt, or molybdenum). For example, each liter of growth medium may be comprised of 1 g $KH_2PO_4$, 1 g $K_2HPO_4$, 1 g $KNO_3$, 1 g NaCl, 0.2 g $MgSO_4$, 26 mg $CaCl_2*2H_2O$, 5.2 mg EDTA $Na_4(H_2O)_2$, 1.5 mg $FeCl_2*4H_2O$, 0.12 mg $CoCl_2*6H_2O$, 0.1 mg $MnCl_2*2H_2O$, 0.07 mg $ZnCl_2$, 0.06 mg $H_3BO_3$, 0.025 mg $NiCl_2*6H_2O$, 0.025 mg $NaMoO_4*2H_2O$, 0.015 mg $CuCl_2*2H_2O$, or a combination thereof. In another embodiment, the growth medium comprises solid and/or liquid media. In yet another embodiment, the growth medium comprises agar.

Methanotrophic microorganisms may be present in the bioreactor in any concentration. Preferably, in one embodiment, there are about 1 to 100 grams of microorganisms per liter of water (or other aqueous solution) in the bioreactor, preferably about 10-250 grams per liter, more preferably about 40-200 grams per liter, over the course of treatment. The methanotrophic microorganisms are exposed to the methane within landfill gas for about 0.1-200 hours, whereupon a portion of the microorganisms within the bioreactor, preferably about 10% to about 50%, are removed, cycled to a subsequent processing phase, according to an embodiment of the invention, inside or outside the bioreactor, and/or optionally replaced with fresh growth media or growth media containing a low concentration of microorganisms, in order to allow more methanotrophic microorganisms to grow or metabolize in the bioreactor and continue to treat the methane within the landfill gas at high rates.

The microorganisms that are removed and/or cycled to a subsequent processing phase inside or outside the bioreactor (depending on the embodiment) are processed further according to the specification of the end-product of microorganism growth. For example, if the microorganism biomass is to be used to generate a polymer such as PHB, the microorganisms may be exposed to a bioreactor receiving a continuous supply of landfill gas and air or oxygen, wherein the growth medium is deprived of a specific essential nutrient, such as nitrogen, in order to cause the microorganisms to synthesize intracellular PHB. After a period of about 0.1 to about 30 hours, some portion of the bioreactor may then be removed in order to harvest the products of bioreactor growth, in this case PHB. PHB may be harvested through a variety of well known harvesting, cell extraction, dewatering, and/or polymer purification techniques. Dewatering methods may include, but are not limited to, the use of centrifuges, spray driers, belt filter presses, freeze drying, fluid bed drying, ribbon drying, flocculation, pressing, and/or filtration. Cell lysis and cell parts separation methods may include, but are not limited to, the use of hot chloroform, sodium hydroxide, cell freezing, sonication, and homogenization. For homogenization, the pressure drop is preferably between about 5000 and about 10,000 bar to effect sufficient cellular lysis. For the use of sodium hydroxide, the concentration of sodium hydroxide is preferably raised to approximately 2 M. If the microorganism biomass is to be used directly as a protein source, the suspended biomass may be dewatered in a belt filter press, bag filter, spray drier, and/or centrifuge, all of which may be used to reduce the water content of the biomass, preferably below about 10% to about 20% total biomass weight. Isolated, dried, and/or harvested microorganism product, such as biomass, polymer, or enzyme, may be used or sold for use.

While the above description of preferred systems and methods of carrying out processes in accordance with embodiments of invention contains many specificities, these should not be construed as limitations on the scope of the invention. As stated, there are a number of ways to carry out a process in accordance with invention. Accordingly, the scope of the invention should be determined not by the preferred systems and methods described, but by the appended claims and their legal equivalents.

What is claimed is:

1. A method for producing a polyhydroxyalkanoate (PHA) in a culture of methanotrophic microorganisms, the method comprising:
   a) providing a gas comprising methane and one or more non-methane substances;
   b) providing a culture of methanotrophic microorganisms;
   c) providing a microorganism culture medium comprising copper and at least-one additional essential nutrient;
   d) exposing said culture to said gas;
   e) allowing the depletion of copper from said culture medium due to metabolization of the copper by the culture of methanotrophic microorganisms, wherein the methanotrophic microorganisms express soluble methane monooxygenase (sMMO) and also express particulate methane monooxygenase (pMMO); and
   f) decreasing the concentration of at least one of said additional essential nutrients, causing said methanotrophic microorganisms to produce said PHA.

2. The method of claim 1, wherein said PHA is selected from the group consisting of polyhydroxybutyrate, polyhydroxybutyrate-covalerate (PHBV), poly-4-hydroxybutyrate (P4HB), polyhydroxyhexanoate (PHHx), and polyhydroxyoctanoate (PHO).

3. The method of claim 1, wherein said step e) is followed by said step f), and wherein step f) followed by step e) comprises a production cycle.

4. The method of claim 3, further comprising repeating step e) followed by step f) one or more times, thereby resulting in at least a first production cycle and a second production cycle.

5. The method of claim 4, wherein the molecular weight of said PHA produced in said first production cycle differs from the molecular weight of said PHA produced in said second production cycle by less than 50%.

6. The method of claim 5, wherein said molecular weight ranges from about 100 to about 5,000,000 Daltons.

7. The method of claim 5, wherein said molecular weight distribution ranges from about 100,000 to about 2,500,000 Daltons.

8. The method of claim 4, wherein the polydispersity of said PHA produced in said first production cycle differs from the polydispersity of said PHA produced in said second production cycle by less than 75%.

9. The method of claim 4, wherein the polydispersity of said PHA produced in said first production cycle differs from the polydispersity of said PHA produced in said second production cycle by less than 50%.

10. The method of claim 8, wherein said polydispersity ranges from about 0.1 to about 5.0.

11. The method of claim 1, wherein said one or more non-methane substances are selected from the group consisting of methanol, acetone, acetate, formate, formaldehyde, hydroxyalkanoates, hydroxybutyrate, octanoic acid, octanol, carbon dioxide, nitrogen, oxygen, di-oxygen, di-nitrogen, water, water vapor, argon, ethane, propane, butyrate, butyric acid, hexanoic acid, hexanol, heptanoic acid, heptanol, pentane, pentanoic acid, and volatile organic compounds.

12. The method of claim 1, wherein said culture comprises two or more species of methanotrophic microorganisms.

13. The method of claim 1, wherein said culture medium further comprises one or more of carbon, hydrogen, oxygen, phosphorus, potassium, calcium, sodium, chlorine, methane, carbon dioxide, magnesium, iron, sulfate, manganese, boron, zinc, aluminum, nickel, chromium, cobalt, or molybdenum.

14. The method of claim 4, wherein the concentration of said pMMO and said sMMO produced in said microorganisms in said first production cycle differs by less than 75% from the total concentration of said pMMO and said sMMO produced in said microorganisms in said second production cycle.

15. The method of claim 1, wherein said gas comprising methane is produced from a landfill, wherein the polyhydroxyalkanoate produced is PHB, wherein said culture of microorganisms is exposed to said gas comprising methane in a bioreactor, and wherein said culture of methanotrophic microorganisms comprises a non-specified consortium of methanotrophic microorganisms.

16. The method of claim 1, wherein said pMMO expressed by said methanotrophic microorganisms represents greater than 80% of said MMO and said sMMO expressed by said methanotrophic microorganisms represent less than 20% of said MMO.

17. The method of claim 1, wherein said pMMO expressed by said methanotrophic microorganisms represents greater than 85% of said MMO and said sMMO expressed by said methanotrophic microorganisms represents less than 15% of said MMO.

18. The method of claim 1, wherein said pMMO expressed by said methanotrophic microorganisms represents greater than 95% of said total MMO and said sMMO expressed by said methanotrophic microorganisms represents less than 5% of said MMO.

* * * * *